US012653453B2

(12) United States Patent
Kawamura

(10) Patent No.: US 12,653,453 B2
(45) Date of Patent: Jun. 16, 2026

(54) DEVICE AND TRAINED NEURAL NETWORK FOR DETERMINING FRACTURE PROBABILITY USING A SOFT PART IMAGE

(71) Applicant: FUJIFILM CORPORATION, Tokyo (JP)

(72) Inventor: Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/614,758

(22) Filed: Mar. 25, 2024

(65) Prior Publication Data

US 2024/0260891 A1 Aug. 8, 2024

Related U.S. Application Data

(63) Continuation of application No. PCT/JP2022/035789, filed on Sep. 26, 2022.

(30) Foreign Application Priority Data

Oct. 1, 2021 (JP) ................................. 2021-162984
Aug. 12, 2022 (JP) ................................. 2022-129051

(51) Int. Cl.
*A61B 6/50* (2024.01)
*A61B 5/00* (2006.01)
(Continued)

(52) U.S. Cl.
CPC .......... *A61B 5/4509* (2013.01); *A61B 5/0035* (2013.01); *A61B 5/055* (2013.01);
(Continued)

(58) Field of Classification Search
CPC ..... A61B 5/4509; A61B 5/0035; A61B 5/055; A61B 5/4566; A61B 5/7267;
(Continued)

(56) References Cited

U.S. PATENT DOCUMENTS

2004/0106868 A1* 6/2004 Liew ...................... A61P 19/00
600/442
2011/0158494 A1* 6/2011 Bar-Shalev ............ A61B 6/032
382/131
(Continued)

FOREIGN PATENT DOCUMENTS

JP 2012-179076 A 9/2012
JP 2015-043959 A 3/2015
(Continued)

OTHER PUBLICATIONS

Nissinen, Tomi, et al. "Detecting pathological features and predicting fracture risk from dual-energy X-ray absorptiometry images using deep learning." Bone reports 14 (2021): 101070 (Year: 2021).*

(Continued)

*Primary Examiner* — Serkan Akar
*Assistant Examiner* — Jason P Gross
(74) *Attorney, Agent, or Firm* — SOLARIS Intellectual Property Group, PLLC

(57) ABSTRACT

A processor is configured to acquire a first and a second radiation image which are acquired by imaging a subject including a bone part and a soft part with radiation having different energy distributions, perform weighting subtraction on the first radiation image and the second radiation image to derive a bone part image representing a bone tissue of the subject and a soft part image representing a soft tissue of the subject, derive a bone mineral density for each pixel in a target bone region of the subject from the bone part image, acquire a pixel value for each pixel of a corresponding region, which corresponds to the target bone region, in the soft part image, and derive a fracture probability of a target bone from the bone mineral density for each pixel in the (Continued)

target bone region and the pixel value for each pixel in the corresponding region.

14 Claims, 15 Drawing Sheets

(51) Int. Cl.
  *A61B 5/055* (2006.01)
  *A61B 6/00* (2024.01)
  *G06T 7/00* (2017.01)
(52) U.S. Cl.
  CPC .......... *A61B 5/4566* (2013.01); *A61B 5/7267* (2013.01); *A61B 5/7275* (2013.01); *A61B 6/505* (2013.01); *A61B 6/5217* (2013.01); *A61B 6/5247* (2013.01); *G06T 7/0012* (2013.01); *G06T 2207/10116* (2013.01); *G06T 2207/20076* (2013.01); *G06T 2207/20081* (2013.01); *G06T 2207/20084* (2013.01); *G06T 2207/20224* (2013.01); *G06T 2207/30012* (2013.01)
(58) Field of Classification Search
  CPC ..... A61B 5/7275; A61B 6/505; A61B 6/5217; A61B 6/5247; A61B 6/482; A61B 6/00; A61B 6/4291; A61B 5/7282; A61B 6/4266; A61B 5/417; A61B 5/4504; G06T 7/0012; G06T 2207/10116; G06T 2207/20076; G06T 2207/20081; G06T 2207/20084; G06T 2207/20224; G06T 2207/30012; G06T 2207/30008; G06T 2207/10081; G06T 5/50; G06T 7/0008; G06T 7/62; G16H 50/30; G01B 15/045; G01B 15/025; G01N 23/046
  See application file for complete search history.

(56) References Cited

U.S. PATENT DOCUMENTS

| | | | |
|---|---|---|---|
| 2016/0140720 A1 | 5/2016 | Naito | |
| 2018/0020999 A1* | 1/2018 | Yamamoto | A61B 6/025 378/4 |
| 2018/0122094 A1 | 5/2018 | Naito | |
| 2018/0374209 A1* | 12/2018 | Patil | G06N 3/0464 |
| 2019/0362492 A1 | 11/2019 | Kawamura | |
| 2020/0401843 A1* | 12/2020 | Peng | A61B 5/7267 |
| 2020/0402226 A1* | 12/2020 | Peng | G06N 20/00 |
| 2021/0369224 A1 | 12/2021 | Okano et al. | |
| 2022/0092785 A1* | 3/2022 | Cant | G06V 10/765 |
| 2022/0147757 A1 | 5/2022 | Peng | |
| 2022/0175335 A1* | 6/2022 | Taki | G16H 30/40 |
| 2022/0358652 A1* | 11/2022 | Torii | A61B 6/5217 |
| 2023/0111463 A1* | 4/2023 | Hoernig | G06T 7/0012 345/418 |
| 2024/0225581 A9* | 7/2024 | Kim | G06T 7/00 |

FOREIGN PATENT DOCUMENTS

| | | |
|---|---|---|
| JP | 2019-202035 A | 11/2019 |
| JP | 2021-002339 A | 1/2021 |
| WO | 2016/129682 A1 | 8/2016 |
| WO | 2016/190327 A1 | 12/2016 |
| WO | 2020/166561 A1 | 8/2020 |

OTHER PUBLICATIONS

Hsieh et al. Automated bone mineral density prediction and fracture risk assessment using plain radiographs via deep learning. Nature communications. Sep. 16, 2021;12(1):5472 (Year: 2021).*
Ho-Le, Thao P., et al. "Prediction of hip fracture in post-menopausal women using artificial neural network approach." 2017 39th Annual International Conference of the IEEE Engineering in Medicine and Biology Society (EMBC). IEEE, 2017 (Year: 2017).*
Hussain, Dildar, and Seung-Moo Han. "Computer-aided osteoporosis detection from DXA imaging." Computer methods and programs in biomedicine 173 (2019): 87-107. (Year: 2019).*
Glaser et al. "Hip Fracture Risk Modelling Using DXA and Deep Learning," slide obtained from https://neurips.cc/virtual/2020/20994; (last visited Nov. 6, 2025); Presented Dec. 2020. (Year: 2020).*
International Search Report issued in International Application No. PCT/JP2022/035789 on Dec. 6, 2022.
Written Opinion of the ISA issued in International Application No. PCT/JP2022/035789 on Dec. 6, 2022.

* cited by examiner

DEVICE AND TRAINED NEURAL NETWORK FOR DETERMINING FRACTURE PROBABILITY USING A SOFT PART IMAGE

CROSS-REFERENCE TO RELATED APPLICATIONS

The present application is a Continuation of PCT International Application No. PCT/JP2022/035789, filed on Sep. 26, 2022, which claims priority to Japanese Patent Application No. 2021-162984, filed on Oct. 1, 2021, and Japanese Patent Application No. 2022-129051, filed on Aug. 12, 2022. Each application above is hereby expressly incorporated by reference, in its entirety, into the present application.

BACKGROUND

Technical Field

The present invention relates to a bone disease prediction device, a method, a program, a learning device, a method, a program, and a trained neural network.

Related Art

Diseases such as fractures and dislocations related to movement organs, such as bones, joints, and muscles, cause a state in which a patient is bedridden. In particular, femoral and vertebral fractures are likely to result in a patient being bedridden. It is known that a five-year survival rate in a case of the patient who is bedridden is lower than a five-year survival rate for cancer. For this reason, various methods for evaluating a movement organ disease, particularly, a fracture risk have been proposed.

For example, JP2019-202035A proposes a method of acquiring bone mineral information representing a bone mineral density of a vertebra from a radiation image to derive a fracture risk from alignment of a spinal column and the bone mineral information. Further, WO2020/166561A proposes a method of calculating a bone mineral density and a muscle mass for each pixel of a radiation image and calculating a statistic value related to a subject based on the bone mineral density and the muscle mass to evaluate the fracture risk based on the statistic value.

On the other hand, it is possible to prevent a bone disease from aggravating by finding signs of the bone disease, such as an initial fracture or an initial bone metastasis of a cancer, and carrying out a treatment at an early stage. The initial sign of the bone disease can be checked by acquiring a magnetic resonance imaging (MRI) image. Regarding the bone disease, a diagnosis is first made by using a simple radiation image of a subject, and in a case where a morphological abnormality of a bone is found, a detailed examination using the MRI image is performed. However, in the bone disease at an initial stage, a morphological change of the bone does not appear or the change is minute even in a case where the morphological change appears. Thus, it is difficult to specify the bone disease at an initial stage in the simple radiation image.

SUMMARY OF THE INVENTION

The present disclosure has been made in view of the above circumstances, and is to specify a bone disease at an initial stage by using a simple radiation image.

A bone disease prediction device according to the present disclosure comprises at least one processor, in which the processor is configured to acquire a first radiation image and a second radiation image which are acquired by imaging a subject including a bone part and a soft part with radiation having different energy distributions, perform weighting subtraction on the first radiation image and the second radiation image to derive a bone part image representing a bone tissue of the subject and a soft part image representing a soft tissue of the subject, derive a bone mineral density for each pixel in a target bone region of the subject from the bone part image, acquire a pixel value for each pixel of a corresponding region, which corresponds to the target bone region, in the soft part image, and derive a fracture probability of a target bone from the bone mineral density for each pixel in the target bone region and the pixel value for each pixel in the corresponding region.

In the bone disease prediction device according to the present disclosure, the processor may be configured to function as a trained neural network subjected to machine learning using, as training data, a bone mineral density for each pixel of a target bone region derived from a bone part image of a human body, a pixel value for each pixel of a corresponding region, which corresponds to the target bone region, derived from a soft part image of the human body, and correct answer data representing a fracture probability of the target bone.

Further, in the bone disease prediction device according to the present disclosure, the processor may be configured to derive the fracture probability from the first radiation image or the second radiation image, in addition to the bone mineral density for each pixel in the target bone region and the pixel value for each pixel in the corresponding region.

Further, in the bone disease prediction device according to the present disclosure, the processor may be configured to function as a trained neural network subjected to machine learning using, as training data, a simple radiation image of a human body, a bone mineral density for each pixel of the target bone derived from a bone part image of the human body, a pixel value for each pixel of a corresponding region, which corresponds to the target bone, derived from a soft part image of the human body, and correct answer data representing the fracture probability.

Further, in the bone disease prediction device according to the present disclosure, the processor may be configured to display the fracture probability on a display.

Further, in the bone disease prediction device according to the present disclosure, the target bone may be a femur.

Further, in the bone disease prediction device according to the present disclosure, the target bone may be a vertebra.

Further, in the bone disease prediction device according to the present disclosure, the processor may be configured to derive the bone part image and the soft part image that have a minimum correlation with each other.

In this case, the processor may be configured to derive the bone part image and the soft part image such that a correlation of specific frequency components in the bone part image and the soft part image is minimized.

A learning device according to the present disclosure comprises at least one processor, in which the processor is configured to perform machine learning on a neural network by using, as training data, a bone mineral density for each pixel of a target bone derived from a bone part image of a human body, a pixel value for each pixel of a corresponding region, which corresponds to the target bone, derived from a soft part image of the human body, and correct answer data representing a fracture probability of the target bone to construct a trained neural network that derives a fracture probability of the target bone of the target subject, from a bone mineral density for each pixel in a target bone region derived from a bone part image of a target subject and a pixel value for each pixel of a corresponding region, which corresponds to the target bone region, derived from a soft part image of the target subject.

In the learning device according to the present disclosure, the processor may be configured to perform the machine learning on the neural network by further using, as training data, a simple radiation image of the human body.

A first trained neural network according to the present disclosure derives, in a case where a bone mineral density for each pixel of a target bone region derived from a bone part image of a target subject and a pixel value for each pixel in a corresponding region, which corresponds to the target bone region, derived from a soft part image of the target subject are input, a fracture probability of a target bone of the target subject.

A second trained neural network according to the present disclosure derives, from a simple radiation image of a target subject, a bone mineral density for each pixel of a target bone region derived from a bone part image of the target subject, and a pixel value for each pixel in a corresponding region, which corresponds to the target bone region, derived from a soft part image of the target subject, a fracture probability of a target bone of the target subject.

A bone disease prediction method comprises acquiring a first radiation image and a second radiation image which are acquired by imaging a subject including a bone part and a soft part with radiation having different energy distributions, performing weighting subtraction on the first radiation image and the second radiation image to derive a bone part image representing a bone tissue of the subject and a soft part image representing a soft tissue of the subject, deriving a bone mineral density for each pixel in a target bone region of the subject from the bone part image;

acquiring a pixel value for each pixel of a corresponding region, which corresponds to the target bone region, in the soft part image; and deriving a fracture probability of a target bone from the bone mineral density for each pixel in the target bone region and the pixel value for each pixel in the corresponding region.

A learning method according to the present disclosure comprises performing machine learning on a neural network by using, as training data, a bone mineral density for each pixel of a target bone derived from a bone part image of a human body, a pixel value for each pixel of a corresponding region, which corresponds to the target bone, derived from a soft part image of the human body, and correct answer data representing a fracture probability of the target bone to construct a trained neural network that derives a fracture probability of the target bone of the target subject, from a bone mineral density for each pixel in a target bone region derived from a bone part image of a target subject and a pixel value for each pixel of a corresponding region, which corresponds to the target bone region, derived from a soft part image of the target subject.

The bone disease prediction method and the learning method according to the present disclosure may be provided as a program for causing a computer to execute the methods.

According to the present disclosure, it is possible to specify the bone disease at an initial stage by using the simple radiation image.

BRIEF DESCRIPTION OF THE DRAWINGS

FIG. 11 is a diagram showing a schematic configuration of a neural network used in the present embodiment.

FIG. 13 is a diagram for describing learning of the neural network.

DETAILED DESCRIPTION

Figure 1:
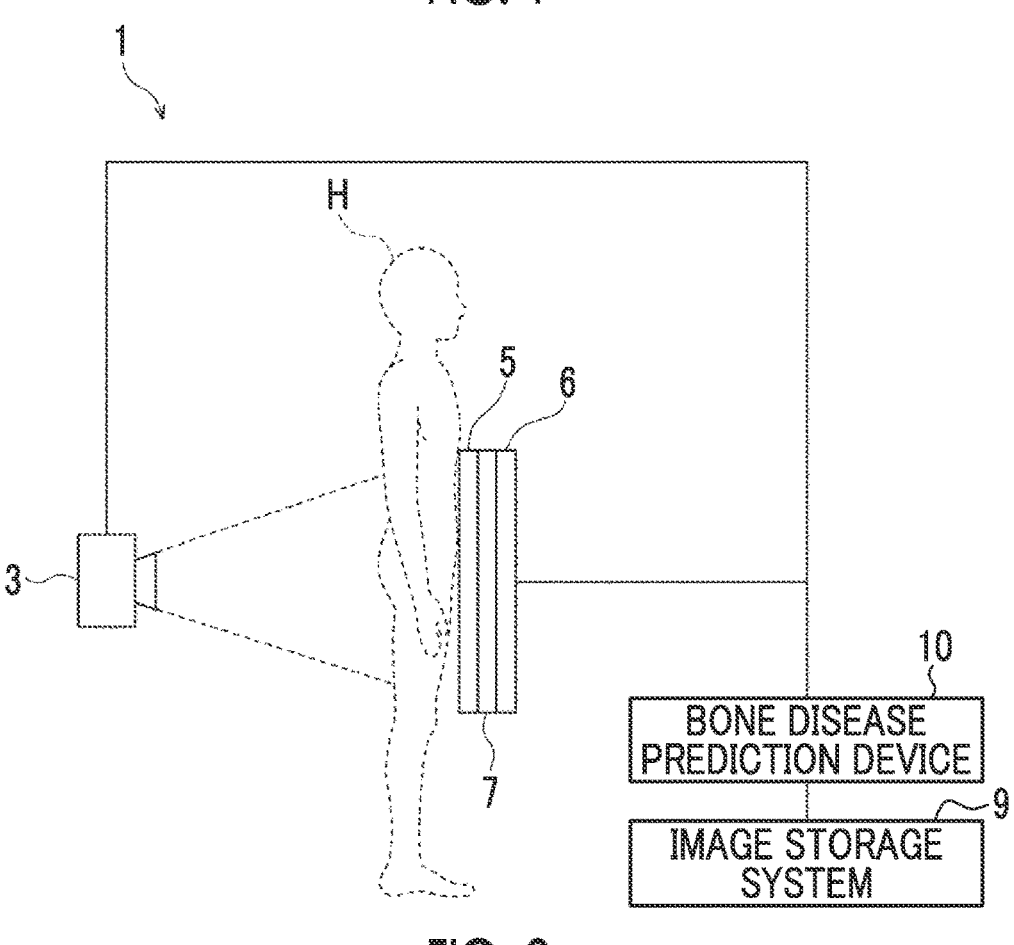
FIG. 1 is a block diagram schematically showing a configuration of a radiation image capturing system to which a bone disease prediction device and a learning device according to an embodiment of the present disclosure are applied.

Hereinafter, embodiments of the present disclosure will be described with reference to drawings. FIG. 1 is a block diagram schematically showing a configuration of a radiation image capturing system to which a bone disease prediction device and a learning device according to an embodiment of the present disclosure are applied. As shown in FIG. 1, the radiation image capturing system according to the present embodiment comprises an imaging apparatus 1 and a bone disease prediction device and learning device 10 (hereinafter, may be represented by bone disease prediction device) according to the present embodiment.

The imaging apparatus 1 is an imaging apparatus for performing energy subtraction by a so-called one-shot method in which radiation, such as an X-ray, emitted from a radiation source 3 and transmitted through a subject H is converted into energy and is emitted to a first radiation detector 5 and a second radiation detector 6. During the imaging, as shown in FIG. 1, the first radiation detector 5, a radiation energy conversion filter 7 made of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

Accordingly, in the first radiation detector 5, a first radiation image G1 of the subject H by low-energy radiation also including a so-called soft ray is acquired. Further, in the second radiation detector 6, a second radiation image G2 of the subject H by high-energy radiation from which the soft ray is removed is acquired. Note that both the first and second radiation images G1 and G2 are two-dimensional images that are transmission images of the subject acquired by simple imaging in which the radiation is emitted to the subject H once. Thus, both the first and second radiation images G1 and G2 are simple radiation images. The first and second radiation images G1 and G2 are input to the bone disease prediction device 10.

The first and second radiation detectors 5 and 6 can perform recording and reading-out of the radiation image repeatedly. A so-called direct-type radiation detector that directly receives the emission of the radiation and generates an electric charge may be used, or a so-called indirect-type radiation detector that converts the radiation into visible light and then converts the visible light into an electric charge signal may be used. Further, as a method of reading out a radiation image signal, it is desirable to use a so-called thin film transistor (TFT) readout method in which a TFT switch is turned on and off to read out the radiation image signal, or a so-called optical readout method in which read out light is emitted to read out the radiation image signal. However, other methods may also be used without being limited to these methods.

Note that the bone disease prediction device 10 is connected to an image storage system 9 via a network (not shown).

The image storage system 9 is a system that stores image data of the radiation image captured by the imaging apparatus 1. The image storage system 9 extracts an image corresponding to a request from the radiation bone disease prediction device 10 from the stored radiation image and transmits the extracted image to a request source device. Specific examples of the image storage system 9 include picture archiving and communication systems (PACS).

Figure 2:
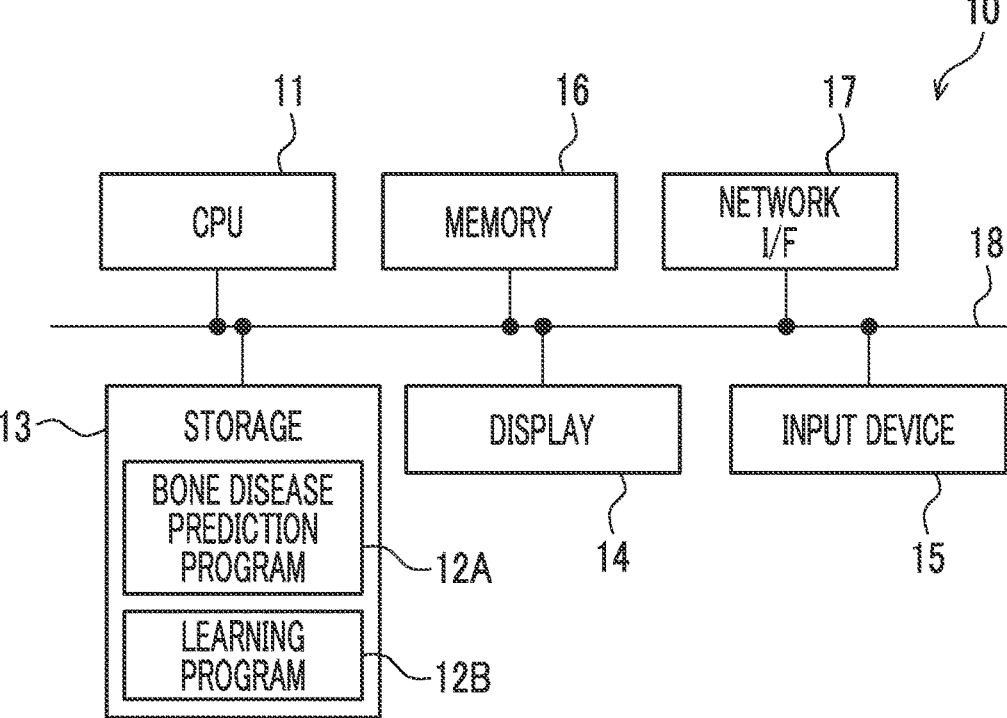
FIG. 2 is a diagram showing a schematic configuration of the bone disease prediction device and the learning device according to an embodiment of the present disclosure.

Next, the bone disease prediction device according to the present embodiment will be described. First, a hardware configuration of the bone disease prediction device according to the present embodiment will be described with reference to FIG. 2. As shown in FIG. 2, the bone disease prediction device 10 is a computer, such as a workstation, a server computer, and a personal computer, and comprises a central processing unit (CPU) 11, a non-volatile storage 13, and a memory 16 as a transitory storage region. Further, the bone disease prediction device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. The CPU 11 is an example of a processor in the present disclosure.

The storage 13 is formed by a hard disk drive (HDD), a solid state drive (SSD), a flash memory, and the like. The storage 13 as a storage medium stores a bone disease prediction program 12A and a learning program 12B installed in the bone disease prediction device 10. The CPU 11 reads out the bone disease prediction program 12A and the learning program 12B from the storage 13, expands the readout programs in the memory 16, and executes the expanded bone disease prediction program 12A and learning program 12B.

The bone disease prediction program 12A and the learning program 12B are stored in a storage device of a server computer connected to the network or a network storage in an accessible state from the outside and are downloaded and installed in the computer configuring the bone disease prediction device 10 in response to a request. Alternatively, the bone disease prediction program 12A and the learning program 12B are distributed in a state of being recorded on a recording medium, such as a digital versatile disc (DVD) or a compact disc read only memory (CD-ROM), and are installed in the computer configuring the bone disease prediction device 10 from the recording medium.

Figure 3:
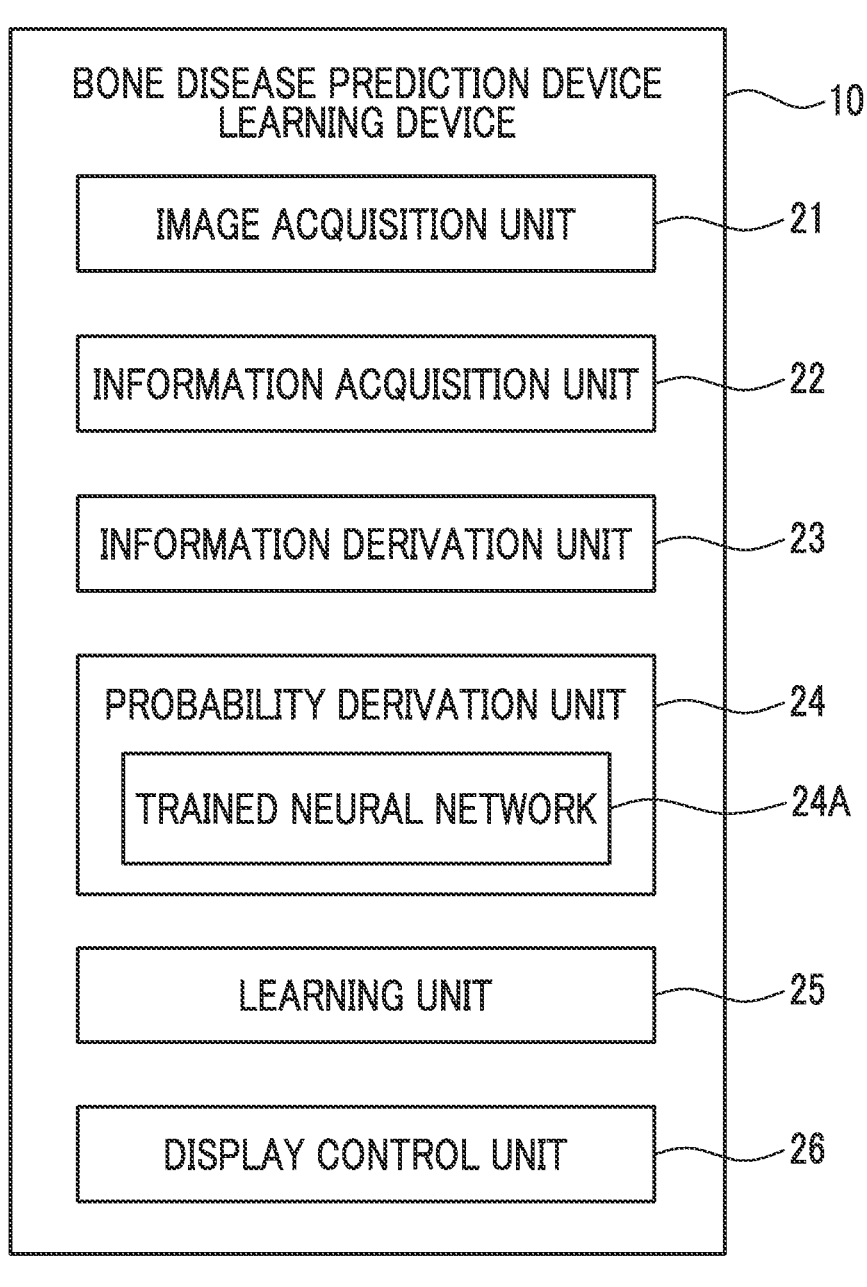
FIG. 3 is a diagram showing a functional configuration of the bone disease prediction device and the learning device according to an embodiment of the present disclosure.

Next, a functional configuration of the bone disease prediction device and the learning device according to the present embodiment will be described. FIG. 3 is a diagram showing the functional configuration of the bone disease prediction device and the learning device according to the present embodiment. As shown in FIG. 3, the bone disease prediction device 10 comprises an image acquisition unit 21, an information acquisition unit 22, an information derivation unit 23, a probability derivation unit 24, a learning unit 25, and a display control unit 26. The CPU 11 executes the bone disease prediction program 12A to function as the image acquisition unit 21, the information acquisition unit 22, the information derivation unit 23, the probability derivation unit 24, and the display control unit 26 and to further function as a trained neural network 24A described below. Further, the CPU 11 executes the learning program 12B to function as the learning unit 25.

The image acquisition unit 21 causes the imaging apparatus 1 to perform the imaging of the subject H to acquire, from the first and second radiation detectors 5 and 6, the first radiation image G1 and the second radiation image G2 which are frontal images of the vicinity of the crotch of the subject H, for example. In acquiring the first radiation image G1 and the second radiation image G2, imaging conditions are set, such as an imaging dose, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid.

The SOD and the SID are used to calculate a body thickness distribution as described below. It is preferable that the SOD is acquired by, for example, a time of flight (TOF) camera. It is preferable that the SID is acquired by, for example, a potentiometer, an ultrasound distance meter, or a laser distance meter.

The imaging condition may be set by an input from the input device 15 by an operator. The set imaging condition is stored in the storage 13.

In the present embodiment, the first and second radiation images G1 and G2 may be acquired by a program separate from the bone disease prediction program 12A and stored in the storage 13. In this case, the image acquisition unit 21 performs the acquisition by reading out the first and second radiation images G1 and G2 stored in the storage 13 from the storage 13 for processing.

The information acquisition unit 22 acquires training data for learning of a neural network, which will be described below, from the image storage system 9 via the network I/F 17.

The information derivation unit 23 derives a bone part image and a soft part image of the subject H from the first and second radiation images G1 and G2. The information derivation unit 23 derives a bone mineral density for each pixel in a target bone region of the subject H from the bone part image, and acquires a pixel value for each pixel of a corresponding region, which corresponds to the target bone region, in the soft part image. In the present embodiment, a target bone is a femur.

Figure 4:
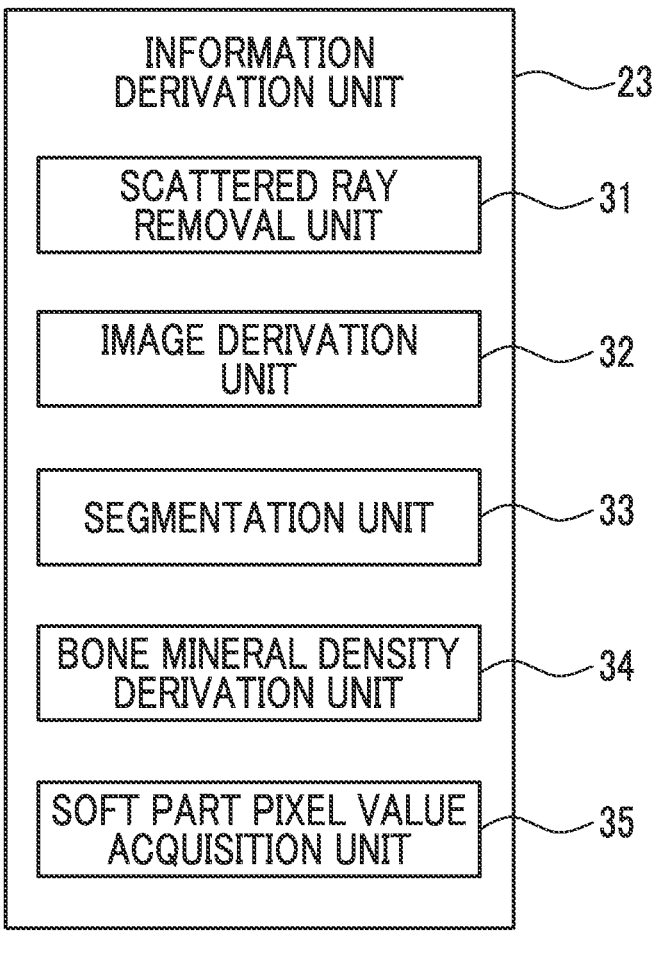
FIG. 4 is a diagram showing a functional configuration of an information derivation unit.

FIG. 4 is a diagram showing a functional configuration of the information derivation unit 23. As shown in FIG. 4, the information derivation unit 23 comprises a scattered ray removal unit 31, an image derivation unit 32, a segmentation unit 33, a bone mineral density derivation unit 34, and a soft part pixel value acquisition unit 35. The CPU 11 executes the bone disease prediction program 12A to function as the scattered ray removal unit 31, the image derivation unit 32, the segmentation unit 33, the bone mineral density derivation unit 34, and the soft part pixel value acquisition unit 35.

Here, each of the first radiation image G1 and the second radiation image G2 includes a scattered ray component based on the radiation scattered in the subject H in addition to a primary ray component of the radiation transmitted through the subject H. Thus, the scattered ray removal unit 31 removes the scattered ray component from the first radiation image G1 and the second radiation image G2. For example, the scattered ray removal unit 31 may apply the method described in JP2015-043959A to remove the scattered ray component from the first radiation image G1 and the second radiation image G2. In a case where the method described in JP2015-043959A or the like is used, the derivation of the body thickness distribution of the subject H and the derivation of the scattered ray component for removing the scattered ray component are performed at the same time.

Hereinafter, the removal of the scattered ray component from the first radiation image G1 will be described, but the removal of the scattered ray component from the second radiation image G2 can also be performed in the same manner. First, the scattered ray removal unit 31 acquires a virtual model K of the subject H having an initial body thickness distribution T0(x,y). The virtual model K is data, which virtually represents the subject H, in which the body thickness according to the initial body thickness distribution T0(x,y) is associated with a coordinate position of each pixel of the first radiation image G1. The virtual model K of the subject H having the initial body thickness distribution T0(x,y) may be stored in advance in the storage 13. Further, a body thickness distribution T(x,y) of the subject H may be calculated based on the SID and the SOD included in the imaging condition. In this case, the body thickness distribution can be obtained by subtracting the SOD from the SID.

Next, the scattered ray removal unit 31 generates, based on the virtual model K, an image in which an estimated primary ray image obtained by estimating a primary ray image to be obtained by imaging the virtual model K is combined with an estimated scattered ray image obtained by estimating a scattered ray image to be obtained by imaging the virtual model K, as an estimated image obtained by estimating the first radiation image G1 obtained by imaging the subject H.

Next, the scattered ray removal unit 31 corrects the initial body thickness distribution T0(x,y) of the virtual model K such that a difference between the estimated image and the first radiation image G1 is small. The scattered ray removal unit 31 repeatedly performs the generation of the estimated image and the correction of the body thickness distribution until the difference between the estimated image and the first radiation image G1 satisfies a predetermined end condition. The scattered ray removal unit 31 derives the body thickness distribution in a case where the end condition is satisfied, as the body thickness distribution T(x,y) of the subject H. Further, the scattered ray removal unit 31 subtracts the scattered ray component in a case where the end condition is satisfied from the first radiation image G1 to remove the scattered ray component included in the first radiation image G1.

Figure 5:
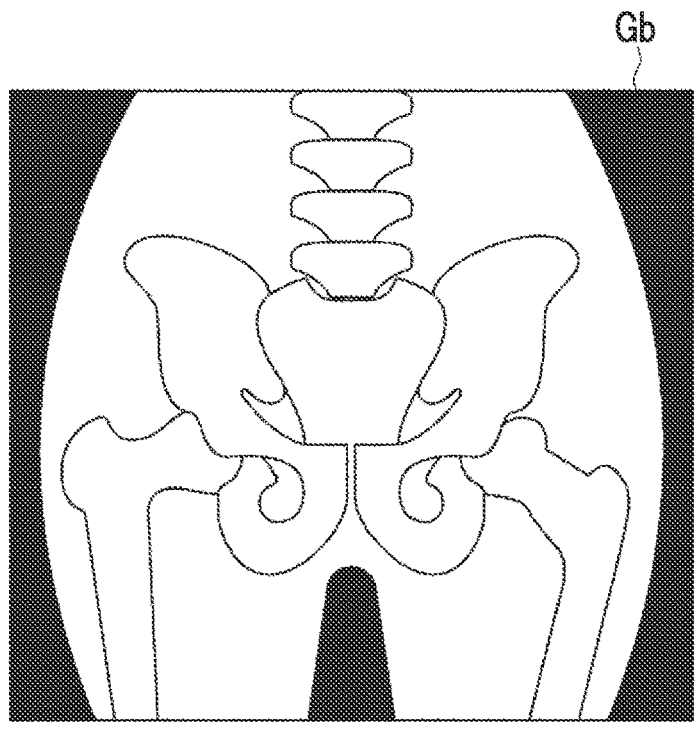
FIG. 5 is a diagram showing a bone part image.

The image derivation unit 32 performs energy subtraction processing to derive, from the first and second radiation images G1 and G2, a bone part image Gb in which a bone part of the subject H is extracted and a soft part image Gs in which a soft part thereof is extracted. Note that, in the first and second radiation images G1 and G2 in the subsequent processing, the scattered ray components are removed. In a case where the bone part image Gb is derived, the image derivation unit 32 performs weighting subtraction on the first and second radiation images G1 and G2 between respectively corresponding pixels, as shown in Expression (1), to derive the bone part image Gb in which the bone part of the subject H included in each of the radiation images G1 and G2 is extracted, as shown in FIG. 5. In Expression (1), $\beta 1$ is a weighting coefficient. The pixel value of each pixel in a bone region of the bone part image Gb is a bone part pixel value.

$$Gb(x, y) = G1(x, y) - \beta 1 \times G2(x, y) \tag{1}$$

Figure 6:
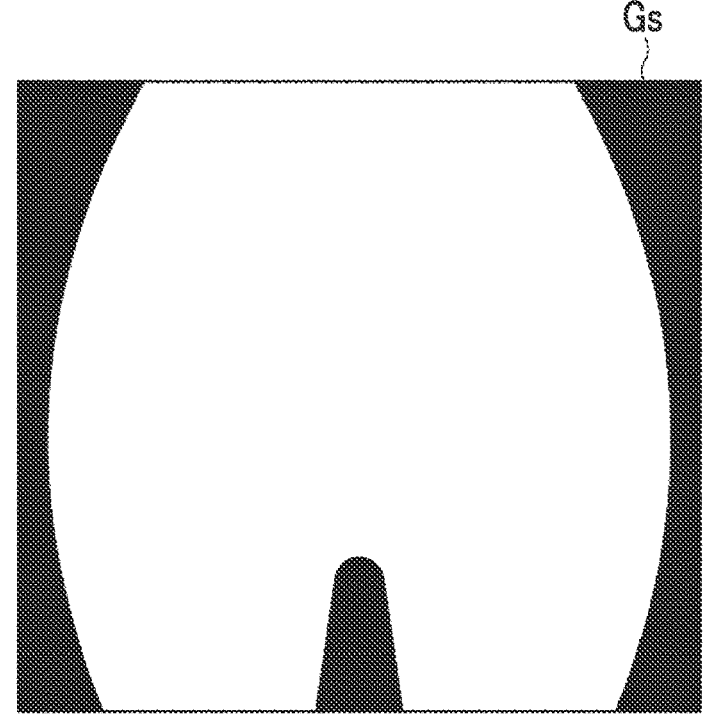
FIG. 6 is a diagram showing a soft part image.

Further, the image derivation unit 32 performs calculation, for example, the weighting subtraction, on the first and second radiation images G1 and G2 between respectively corresponding pixels, as shown in Expression (2), to derive the soft part image Gs in which only the soft part of the subject H included in each of the radiation images G1 and G2 is extracted, as shown in FIG. 6. In Expression (2), $\beta 2$ is a weighting coefficient.

$$Gs(x, y) = G1(x, y) - \beta 2 \times G2(x, y) \tag{2}$$

The soft part image Gs represents a soft region due to a soft tissue of the subject H. In the present embodiment, the "soft tissue" of the subject H refers to a tissue other than a bone tissue, and specifically includes a muscle tissue, a fat tissue, blood, and moisture.

The segmentation unit 33 segments the bone part image Gb into a femoral region, a pelvis region, and a vertebral region. The segmentation may be performed by using an extraction model in which machine learning is performed to respectively extract the femur, the pelvis, and the vertebra from the bone part image Gb. Further, templates respectively representing the femur, the pelvis, and the vertebra may be stored in the storage 13, and template matching between these templates and the bone part image Gb may be performed to perform the segmentation.

Figure 7:
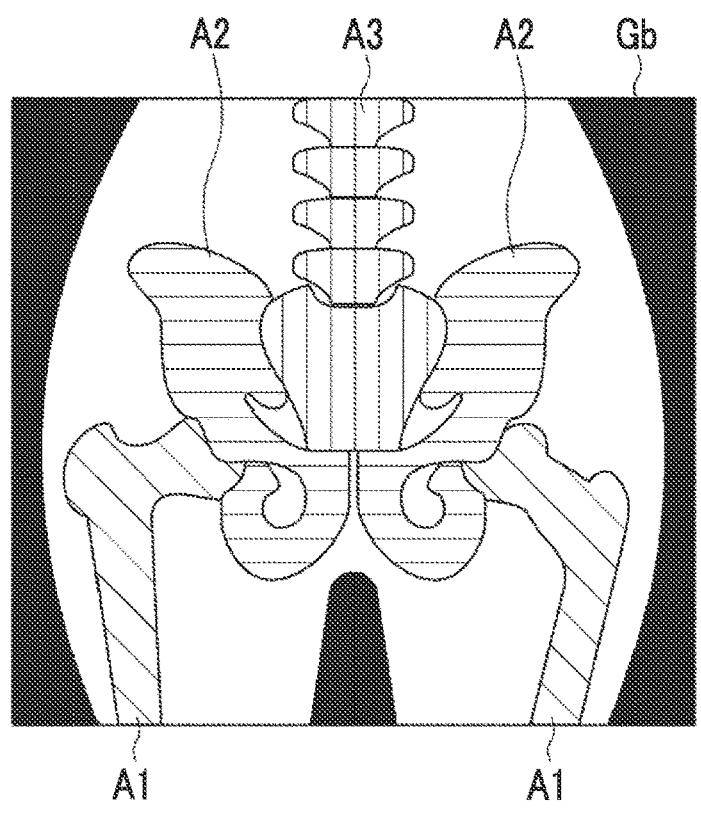
FIG. 7 is a diagram showing a result of segmentation.

FIG. 7 is a diagram showing a result of the segmentation by the segmentation unit 33. As shown in FIG. 7, the bone region in the bone part image Gb is segmented into a femoral region A1, a pelvis region A2, and a vertebral region A3. In FIG. 7, the result of the segmentation is shown by applying different hatching to the femoral region A1, the pelvis region A2, and the vertebral region A3.

On the other hand, regarding the vertebra, the bone part image Gb includes only a sacral vertebra and a lumbar vertebra. The lumbar vertebra is anatomically classified into L5, L4, L3, L2, and L1 from a pelvis side toward the neck. Therefore, it is preferable that the segmentation unit 33 segments the sacral vertebra and the five lumbar vertebras into different regions.

Note that the segmentation unit 33 may segment only the target bone in the bone part image Gb. For example, since the femur is used as the target bone in the present embodiment, only the femoral region A1 may be segmented.

The bone mineral density derivation unit 34 derives the bone mineral density for each pixel of the target bone region, which is a region of the target bone in the bone part image Gb. In the present embodiment, the bone mineral density derivation unit 34 converts each pixel value in the target bone region of the bone part image Gb into a pixel value of a bone part image in a case of being acquired under a reference imaging condition to derive the bone mineral density for each pixel of the target bone region. More specifically, the bone mineral density derivation unit 34 corrects each pixel value of the target bone region using a correction coefficient acquired from a look-up table, which will be described below, to derive the bone mineral density.

Here, a contrast between the soft part and the bone part in the radiation image is lower as the tube voltage in the radiation source 3 is higher and the energy of the radiation emitted from the radiation source 3 is higher. Further, in a procedure in which the radiation transmits through the subject H, a low-energy component of the radiation is absorbed by the subject H, and beam hardening occurs in which the energy of the radiation is increased. The increase in the energy of the radiation due to the beam hardening is larger as the body thickness of the subject H is larger.

Figure 8:
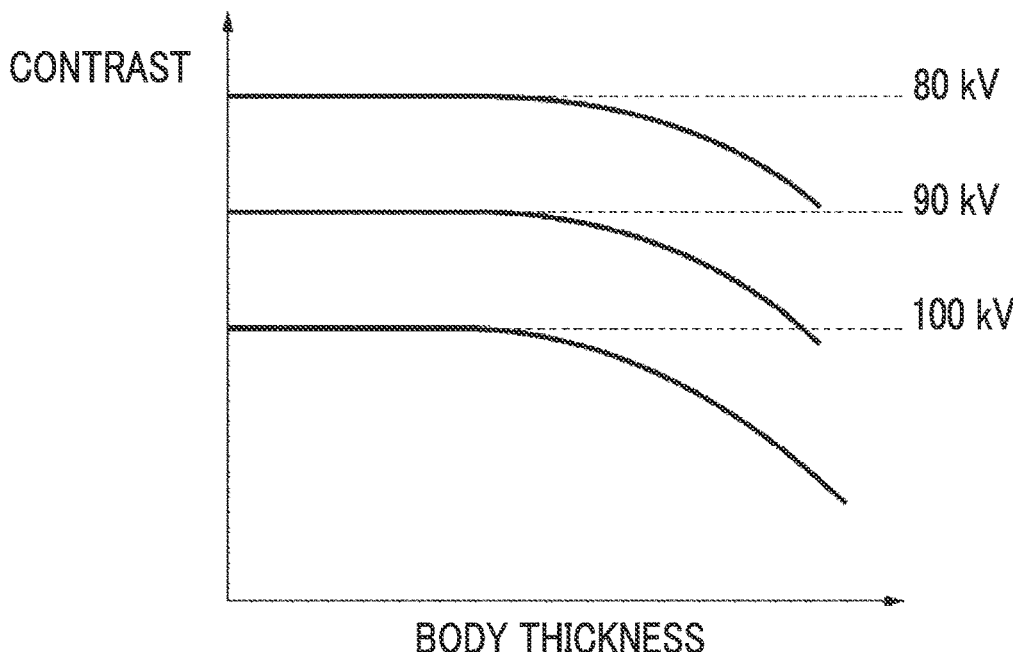
FIG. 8 is a graph showing a relationship between a contrast between a bone part and a soft part and a body thickness of a subject.

FIG. 8 is a graph showing a relationship between the contrast between the bone part and the soft part and the body thickness of the subject H. Note that FIG. 8 shows the relationship between the contrast between the bone part and the soft part and the body thickness of the subject H at three tube voltages of 80 kV, 90 kV, and 100 kV. As shown in FIG. 8, the contrast is lower as the tube voltage is higher. Further, in a case where the body thickness of the subject H exceeds a certain value, the contrast is lower as the body thickness is larger. The contrast between the bone part and the soft part is higher as the pixel value of the bone region in the bone part image Gb is larger. For this reason, the relationship shown in FIG. 8 is shifted to a higher contrast side as the pixel value of the bone region in the bone part image Gb is larger.

In the present embodiment, the storage 13 stores the look-up table for acquiring the correction coefficient for correcting the difference in the contrast according to the tube voltage during imaging and the decrease in the contrast due to the influence of the beam hardening, in the bone part image Gb. The correction coefficient is a coefficient for correcting each pixel value of the bone part image Gb.

Figure 9:
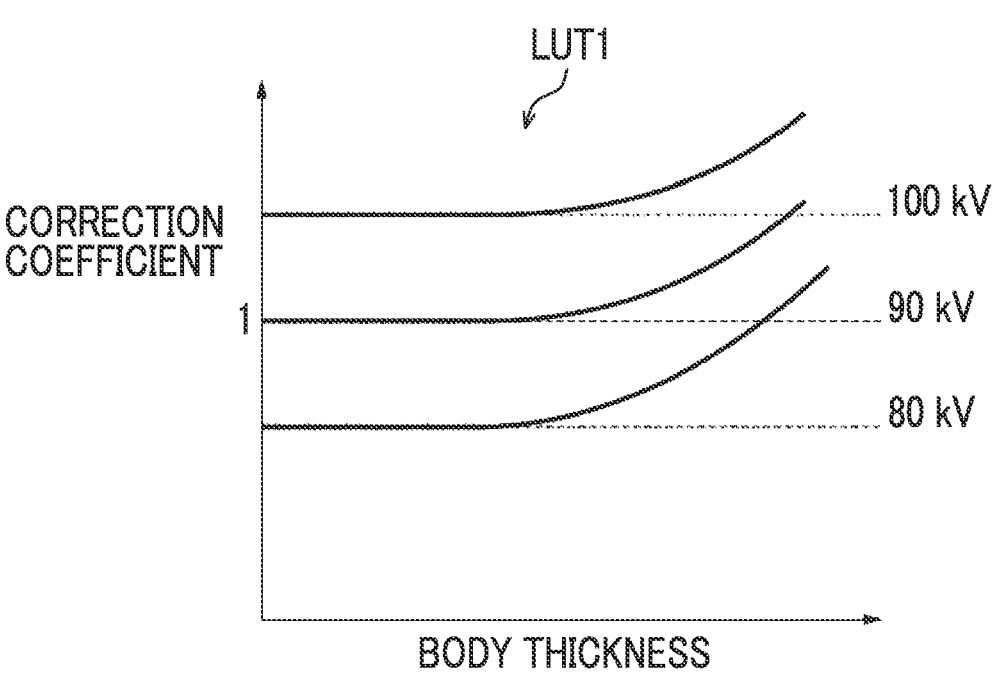
FIG. 9 is a graph showing an example of a look-up table.

FIG. 9 is a graph showing an example of the look-up table stored in the storage 13. FIG. 9 illustrates a look-up table LUT1 in which the reference imaging condition is set to the tube voltage of 90 kV. As shown in FIG. 9, in the look-up table LUT1, a larger correction coefficient is set as the tube voltage is higher and the body thickness of the subject H is larger. In the example shown in FIG. 9, the reference imaging condition is the tube voltage of 90 kV. Thus, in a case where the tube voltage is 90 kV and the body thickness is zero, the correction coefficient is one. Although the look-up table LUT1 is shown in two dimensions in FIG. 9, the correction coefficient differs depending on the pixel value of the bone region. Therefore, the look-up table LUT1 is actually a three-dimensional table to which an axis representing the pixel value of the bone region is added.

The bone mineral density derivation unit 34 extracts, from the look-up table LUT1, the body thickness distribution T(x,y) of the subject H and a correction coefficient $C0(x,y)$ for each pixel according to the imaging condition including a set value of the tube voltage stored in the storage 13. As shown in Expression (3) described below, the bone mineral density derivation unit 34 multiplies each pixel (x,y) of the target bone region in the bone part image Gb by the correction coefficient $C0(x,y)$ to derive a bone mineral density B(x,y) (g/cm$^2$) for each pixel in the target bone region. The bone mineral density B(x,y) derived in this manner represents the pixel value of the bone region included in the radiation image that is acquired by imaging the subject H at the tube voltage of 90 kV, which is the reference imaging condition, and from which the influence of beam hardening is removed.

$$B(x, y) = C0(x, y) \times Gb(x, y) \qquad (3)$$

The soft part pixel value acquisition unit 35 acquires a pixel value Gs(x,y) for each pixel of the corresponding region, which corresponds to the target bone region, in the soft part image Gs. In the present embodiment, the target bone is the femur. Therefore, as shown in FIG. 10, the soft part pixel value acquisition unit 35 acquires the pixel value Gs(x,y) for each pixel of the corresponding region A11 corresponding to the femoral region in the soft part image Gs.

Here, bones include bone marrow. The bone marrow contains a hematopoietic cell. In a case where the hematopoietic cell is over 20 years old, a fat component increases with age. The bone marrow in which the fat component has increased is referred to as adipose marrow. On the other hand, in a case where an initial fracture occurs due to application of pressure to a bone, it is known that inflammation is caused in the bone marrow, and thus the water increases. Since a radiation absorption rate of water is larger than the radiation absorption rate of fat, the water has a higher concentration (that is, is darker) than the fat in the simple radiation image. The bone marrow is the soft tissue. Thus, in a case where inflammation occurs in the bone, the pixel value of the corresponding region in the soft part image Gs, which corresponds to a region of the bone, is increased (that is, darkened) due to the influence of the water. In the present embodiment, in order to capture a sign of an initial fracture based on a change in the concentration of the bone marrow region, the soft part pixel value acquisition unit 35 acquires the pixel value Gs(x,y) for each pixel of the corresponding region, which corresponds to the target bone region, in the soft part image Gs.

Figure 10:
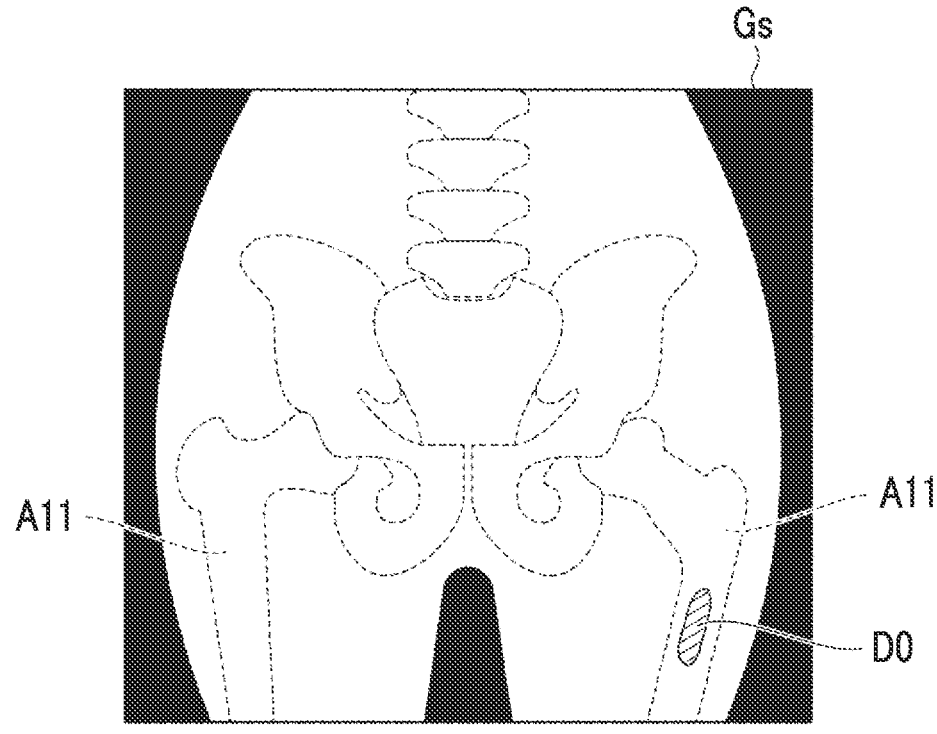
FIG. 10 is a diagram showing setting of a region around a femur in the soft part image.

In FIG. 10, it is shown by hatching that a left femur of the patient includes a region DO having a higher density than the other region.

The probability derivation unit 24 derives a fracture probability of the target bone from the bone mineral density B(x,y) for each pixel of the target bone region and the pixel value Gs(x,y) for each pixel of the corresponding region. For this purpose, in a case where the bone mineral density B(x,y) for each pixel of the target bone region and the pixel value Gs(x,y) for each pixel of the corresponding region are input, the probability derivation unit 24 derives the fracture probability of the target bone by using the trained neural network 24A that outputs the fracture probability of the target bone.

The learning unit 25 performs the machine learning on the neural network by using, as the training data, the bone mineral density for each pixel of the target bone region derived from the bone part image of a human body, the pixel value for each pixel of the corresponding region, which corresponds to the target bone region, derived from the soft part image of the human body, and correct answer data representing the fracture probability of the target bone to construct the trained neural network 24A.

Examples of the neural network include a simple perceptron, a multilayer perceptron, a deep neural network, a convolutional neural network, a deep belief network, a recurrent neural network, and a probabilistic neural network. In the present embodiment, the convolutional neural network is used as the neural network.

Figure 11:
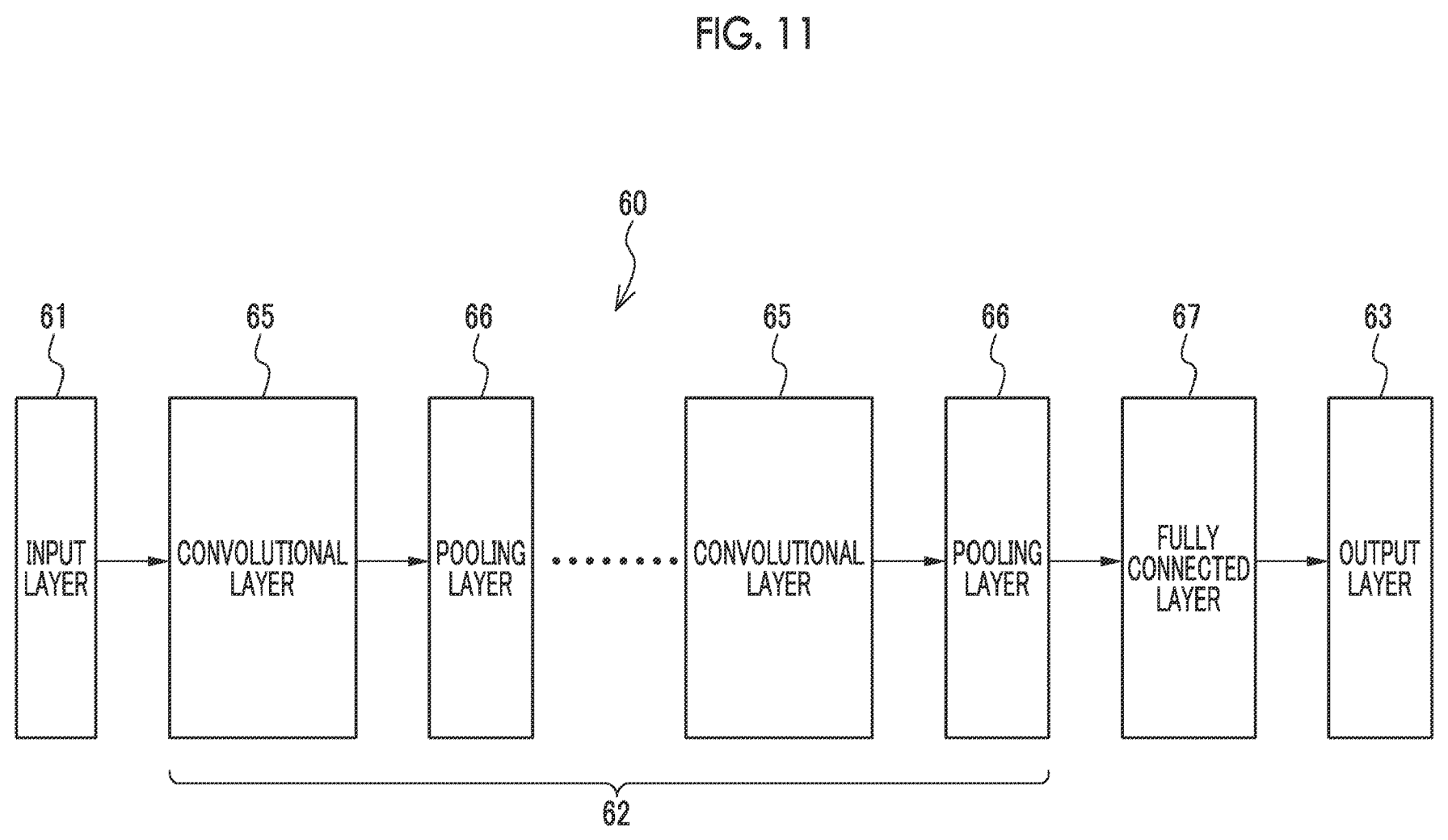

FIG. 11 is a diagram showing the neural network used in the present embodiment. As shown in FIG. 11, a neural network 60 comprises an input layer 61, an interlayer 62, and an output layer 63. The interlayer 62 comprises, for example, a plurality of convolutional layers 65, a plurality of pooling layers 66, and a fully connected layer 67. In the neural network 60, the fully connected layer 67 is present in a previous stage of the output layer 63. In the neural network 60, the convolutional layer 65 and the pooling layer 66 are alternately disposed between the input layer 61 and the fully connected layer 67.

Note that a configuration of the neural network 60 is not limited to the example of FIG. 11. For example, the neural network 60 may comprise one convolutional layer 65 and one pooling layer 66 between the input layer 61 and the fully connected layer 67.

Figure 12:
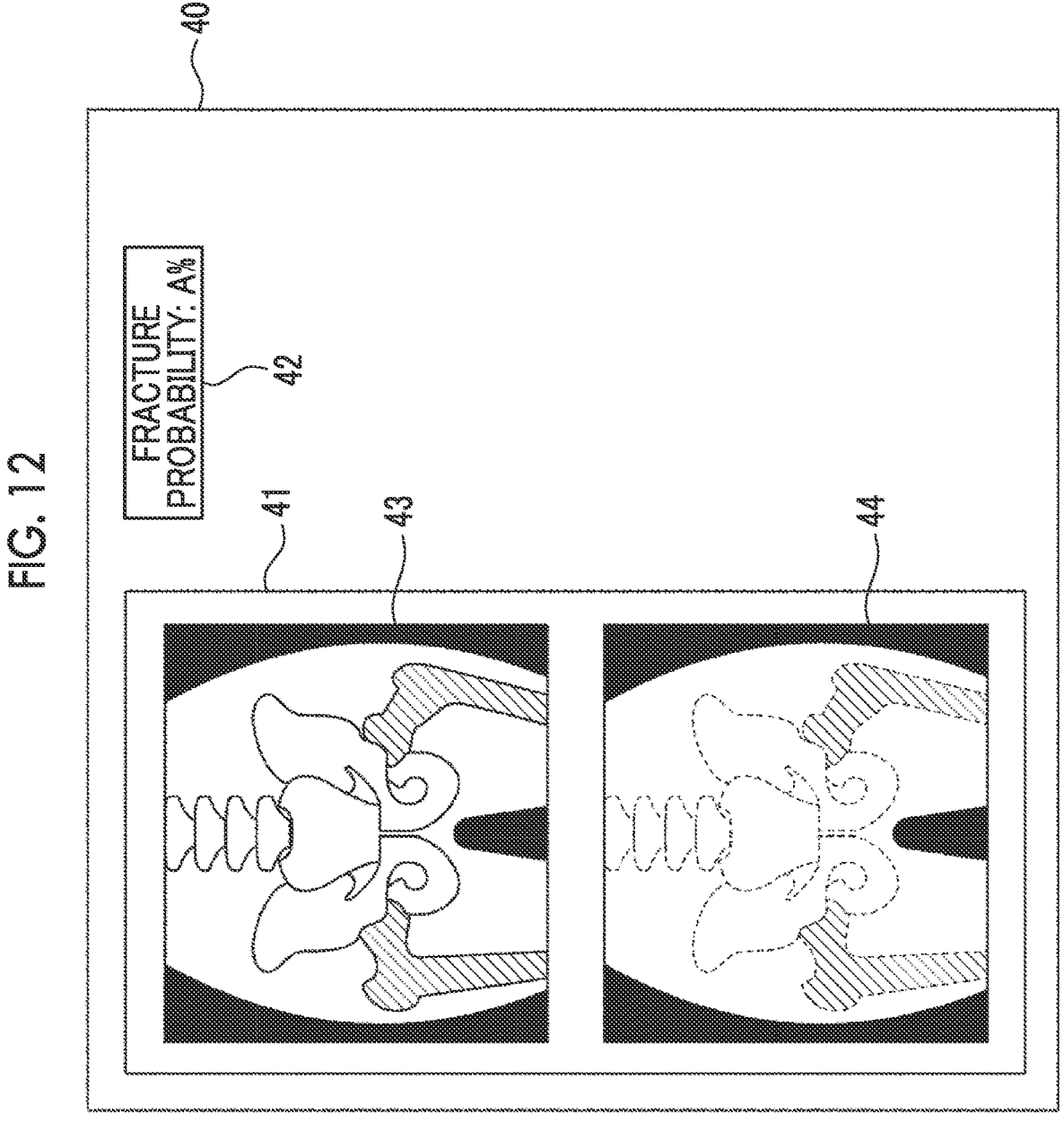
FIG. 12 is a diagram showing training data.

FIG. 12 is a diagram showing an example of the training data used for the learning of the neural network. As shown in FIG. 12, training data 40 consists of data for learning 41 and correct answer data 42. The data for learning 41 consists of a bone mineral density 43 for each pixel of the target bone region in the bone part image and a pixel value 44 for each pixel of the corresponding region in the soft part image, which corresponds to the target bone region. The bone mineral density 43 is derived from the bone part image Gb of the patient in which the initial fracture develops. The pixel value 44 is acquired from the soft part image Gs of the patient in which the initial fracture develops. In this case, the presence or absence of the initial fracture of the patient can be checked by acquiring an MRI image of the patient and interpreting the MRI image. Therefore, the bone part image Gb from which the bone mineral density 43 is derived and the soft part image Gs from which the pixel value 44 is acquired are derived from the radiation image acquired by performing the energy subtraction imaging on the patient in which the initial fracture is found as a result of interpreting the MRI image.

In FIG. 12, the target bone region (femur) in the bone part image is hatched to indicate the bone mineral density in the bone mineral density 43. Further, the corresponding region in the soft part image is hatched to indicate the pixel value in the pixel value 44. The correct answer data 42 consists of the fracture probability.

The training data 40 is derived by recording, for a plurality of patients, statistics in a case where the fracture occurs, regarding the bone mineral density for each pixel of the target bone region and the pixel value for each pixel of the corresponding region, and is stored in the image storage system 9. The fracture probability, which is the correct answer data 42 in the training data 40, can be calculated by obtaining, for the plurality of patients with similar bone mineral density for each pixel of the target bone region and pixel value for each pixel of the corresponding region, the number of cases in which the fracture has occurred after the elapse of a predetermined number of years (for example, one year, two years, or five years) and dividing the obtained number of cases by the number of patients.

Note that the bone mineral density 43 and the pixel value 44, which are the data for learning 41, may be derived by processing the radiation image of a healthy person according to the sign of the initial fracture. Accordingly, it is possible to increase the number of pieces of training data and thus effectively promote the learning. In this case, the fracture probability for the patient presenting with a case similar to the processed radiation image may be used as the correct answer data 42.

Figure 13:
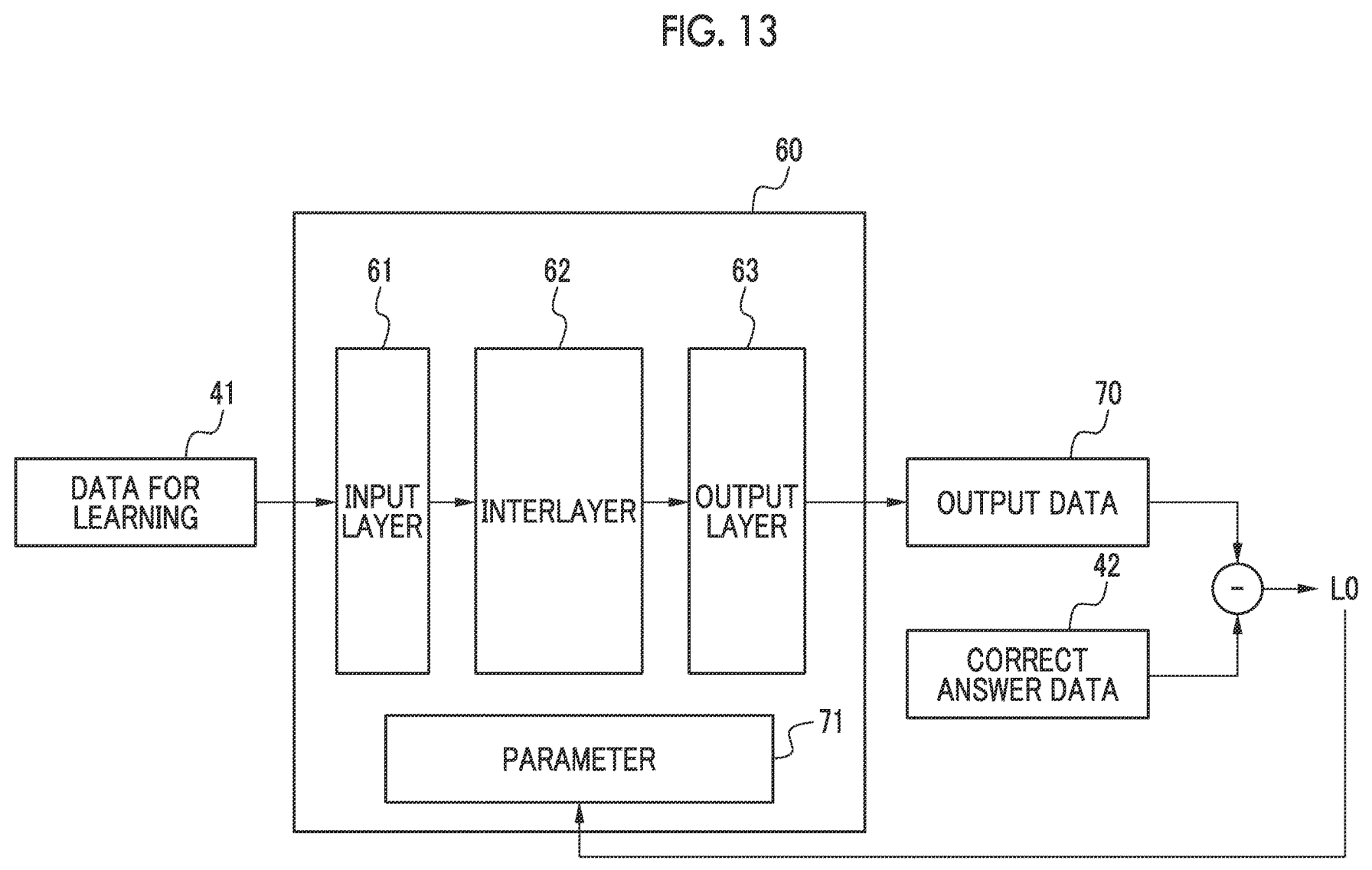

The learning unit 25 performs the learning of the neural network using a large amount of the training data 40. FIG. 13 is a diagram for describing the learning of the neural network 60. In a case where the learning of the neural network 60 is performed, the learning unit 25 inputs the data for learning 41 to the input layer 61 of the neural network 60. The learning unit 25 outputs the fracture probability as output data 70 from the output layer 63 of the neural network 60. The learning unit 25 derives a difference between the output data 70 and the fracture probability included in the correct answer data 42 as a loss L0.

The learning unit 25 performs the learning of the neural network 60 based on the loss L0. Specifically, the learning unit 25 adjusts a kernel coefficient in the convolutional layer 65, a weight of the connection between the respective layers, a weight of the connection in the fully connected layer 67, and the like (hereinafter referred to as parameter 71) such that the loss L0 is small. As a method of adjusting the parameter 71, for example, a backpropagation method can be used. The learning unit 25 repeats the adjustment of the parameter 71 until the loss L0 is equal to or less than a predetermined threshold value. Accordingly, in a case where the bone mineral density for each pixel of the target bone region and the pixel value for each pixel of the corresponding region are input, the parameter 71 is adjusted such that a more accurate fracture probability is output to construct the trained neural network 24A. The constructed trained neural network 24A is stored in the storage 13.

Figure 14:
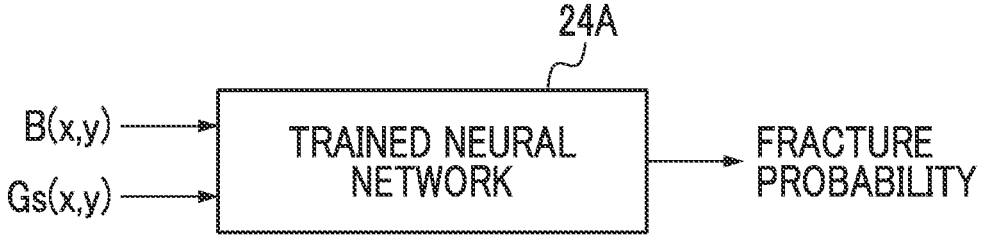
FIG. 14 is a diagram showing an example of a trained neural network.

In a case where the bone mineral density B(x,y) for each pixel of the target bone region, which is derived from the bone part image of the subject H who is a patient, and the pixel value Gs(x,y) for each pixel of the corresponding region, which is acquired from the soft part image of the subject H, are input to the trained neural network 24A constructed in this manner, as shown in FIG. 14, the trained neural network 24A outputs a future fracture probability of the subject H due to the initial fracture of the femur.

Figure 15:
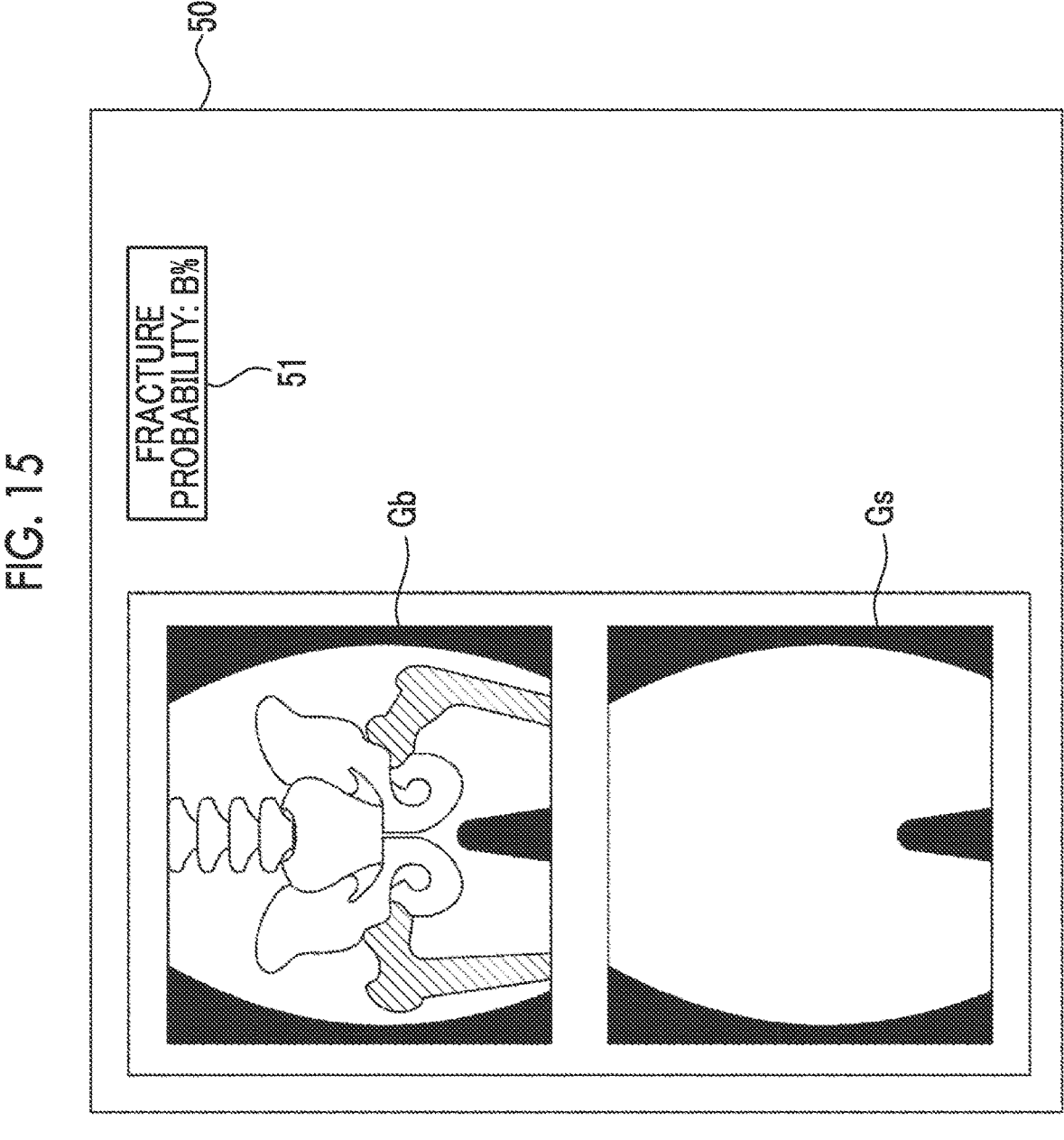
FIG. 15 is a diagram showing a display screen.

The display control unit 26 displays the fracture probability derived by the probability derivation unit 24 on the display 14. FIG. 15 is a diagram showing a display screen of the fracture probability. As shown in FIG. 15, a display screen 50 displays the bone part image Gb, the soft part image Gs, and a fracture probability 51 of the subject H.

Figure 16:
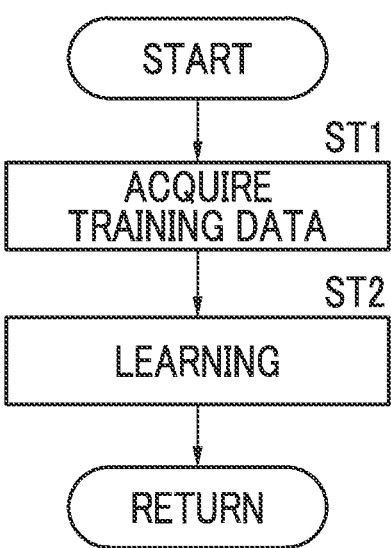
FIG. 16 is a flowchart showing learning processing performed in the present embodiment.

Next, processing performed in the present embodiment will be described. FIG. 16 is a flowchart showing learning processing performed in the present embodiment. First, the information acquisition unit 22 acquires the training data from the image storage system 9 (step ST1), the learning unit 25 inputs the data for learning 41, which is included in the training data 40, to the neural network 60 and causes the neural network 60 to output the fracture probability to perform the learning of the neural network 60 using the loss L0 based on the difference from the correct answer data 42 (step ST2), and the processing returns to step ST1. The learning unit 25 repeats the processing in steps ST1 and ST2 until the loss L0 reaches the predetermined threshold value and ends the learning. The learning unit 25 may repeat the learning a predetermined number of times and end the learning. With the above, the learning unit 25 constructs the trained neural network 24A.

Figure 17:
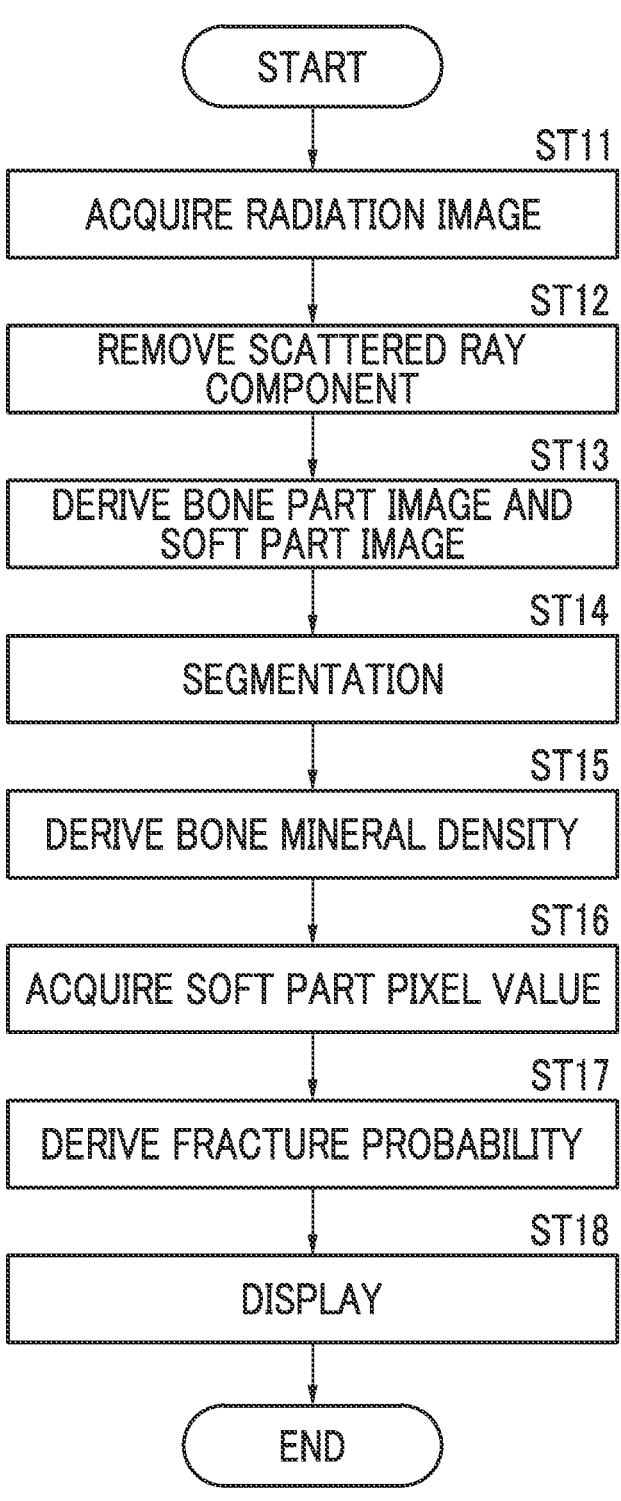
FIG. 17 is a flowchart showing bone disease prediction processing performed in the present embodiment.

Next, bone disease prediction processing according to the present embodiment will be described. FIG. 17 is a flowchart showing the bone disease prediction processing in the present embodiment. Note that the first and second radiation images G1 and G2 are acquired by the imaging and stored in the storage 13. In a case where an instruction to start the processing is input from the input device 15, the image acquisition unit 21 acquires the first and second radiation images G1 and G2 from the storage 13 (radiation image acquisition; step ST11). Next, the scattered ray removal unit 31 of the information derivation unit 23 removes the scattered ray components from the first and second radiation images G1 and G2 (step ST12). Further, the image derivation unit 32 derives the bone part image Gb in which the bone part of the subject H is extracted and the soft part image Gs in which the soft part of the subject H is extracted, from the first and second radiation images G1 and G2 (step ST13). Furthermore, the segmentation unit 33 segments the bone part image Gb into the femoral region, which is the target bone (step ST14).

Subsequently, the bone mineral density derivation unit 34 derives the bone mineral density for each pixel of the target bone region in the bone part image Gb (step ST15), and the soft part pixel value acquisition unit 35 acquires, from the soft part image Gs, the soft part pixel value for each pixel of the corresponding region (step ST16).

Further, the probability derivation unit 24 derives the fracture probability related to the target bone, from the bone mineral density for each pixel of the target bone region and the pixel value for each pixel of the corresponding region, using the trained neural network 24A (step ST17). The display control unit 26 displays the fracture probability derived by the probability derivation unit 24 on the display 14 (step ST18), and the processing ends.

Here, the bone marrow contains the hematopoietic cell. In a case where the hematopoietic cell is over 20 years old, the fat component increases with age. Further, in a case where the initial fracture occurs, inflammation is caused in the bone marrow, and thus the water increases. Since a radiation absorption rate of water is larger than the radiation absorption rate of fat, the water has a higher concentration (that is, is darker) than the fat in the simple radiation image. The bone marrow is the soft tissue. Thus, in a case where inflammation occurs in the bone, the pixel value of the corresponding region in the soft part image Gs, which corresponds to a region of the bone, is increased (that is, darkened) due to the influence of the water.

In the present embodiment, the fracture probability related to the target bone is derived from the bone mineral density B(x,y) for each pixel of the target bone region and the pixel value Gs(x,y) for each pixel of the corresponding region, which corresponds to the target bone region, in the soft part image Gs. In this manner, since the fracture probability is derived by using the pixel value Gs(x,y) of the corresponding region, which corresponds to the target bone region, in the soft part image Gs, it is possible to derive the fracture probability that reflects the sign of the initial fracture. Therefore, with reference to the fracture probability, it is possible to specify a bone disease at an initial stage by using the simple radiation image.

Further, with the display of the fracture probability, it is possible to easily recognize the fracture probability in the current situation.

Figure 18:
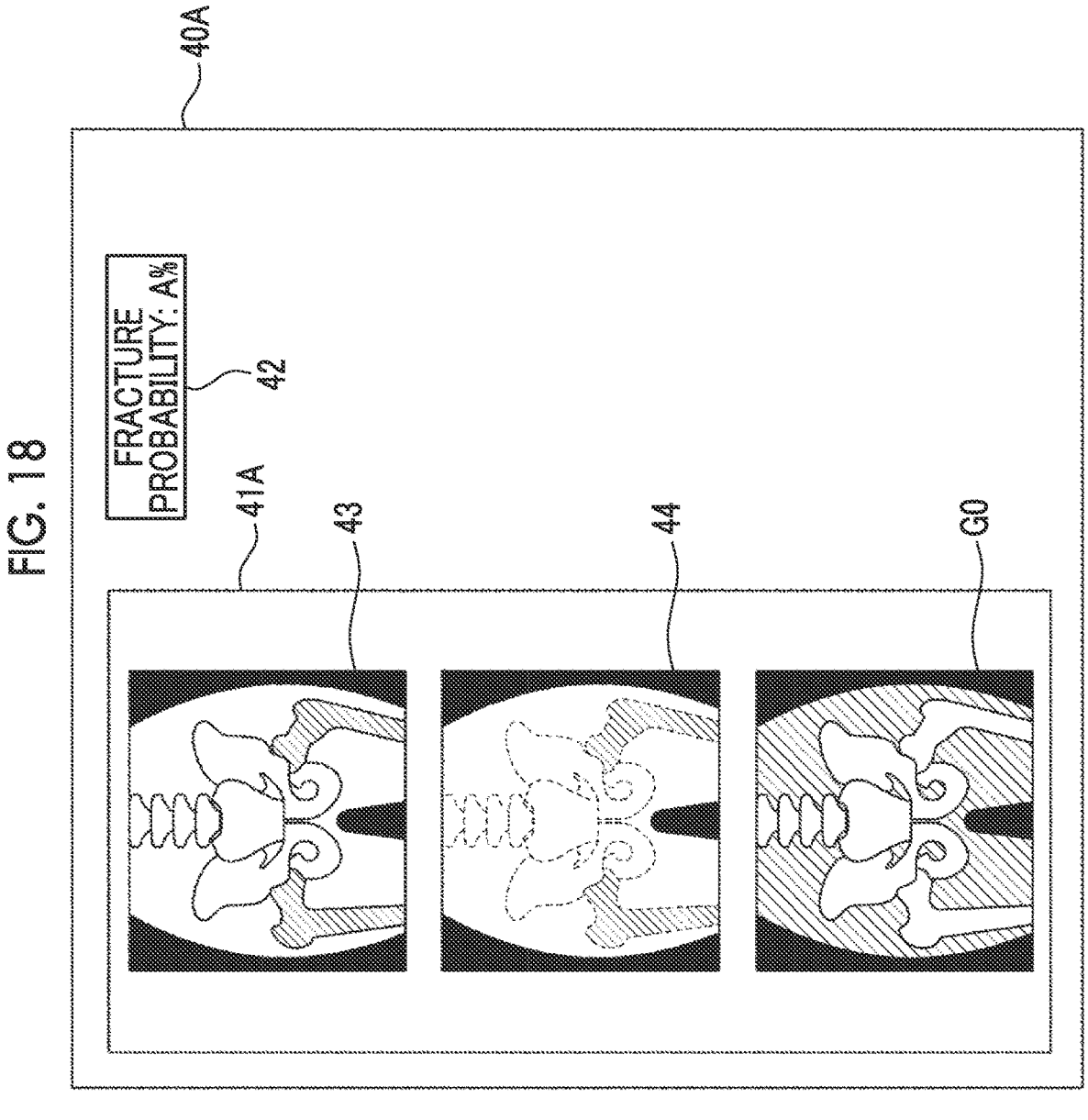
FIG. 18 is a diagram showing another example of the training data.

Note that, in the embodiment described above, the trained neural network 24A is constructed by using the training data 40 including the data for learning 41 consisting of the bone mineral density 43 for each pixel of the target bone region in the bone part image and the pixel value 44 for each pixel of the corresponding region, which corresponds to the target bone region, in the soft part image, but the present disclosure is not limited thereto. As shown in FIG. 18, the trained neural network 24A may be constructed by further using training data 40A including, as data for learning 41A, a simple radiation image G0. In a case where the trained neural network 24A constructed as described above is used, in addition to the bone mineral density for each pixel of the target bone region of the subject H and the pixel value for each pixel of the corresponding region, the first radiation image G1 or the second radiation image G2 of the subject H is input to the trained neural network 24A to derive the fracture probability.

Further, in the embodiment described above, the femur is used as the target bone, but the present disclosure is not limited thereto. The vertebra may be used as the target bone.

Particularly, the bone mineral density of the vertebra is reduced due to occurrence of osteoporosis. In a case where the osteoporosis worsens, the vertebra is compressed and deformed in the vertical direction of the human body, and further is compression fractured. For this reason, in a case where the target bone is the vertebra, with the use of the bone mineral density of the vertebra, which is the target bone, and the pixel value of the corresponding region corresponding to the vertebra, it is possible to capture the sign of the initial fracture more accurately to predict a fracture occurrence probability.

Further, in the present embodiment, in addition to the femur and the vertebra, any bone such as the femur and a shinbone around a knee joint can be used as the target bone.

In the embodiment described above, the trained neural network 24A is constructed by using, as the data for learning 41, the bone mineral density 43 for each pixel of the target bone region and the pixel value 44 for each pixel of the corresponding region corresponding to the target bone region, which are acquired from the radiation image of the patient in which the bone marrow is inflamed due to the development of the initial fracture. However, the present disclosure is not limited thereto. The trained neural network 24A may be constructed by using, as the data for learning 41, the bone mineral density for each pixel of the target bone region and the pixel value for each pixel of the corresponding region corresponding to the target bone region, which are acquired from the radiation image of a patient in which a bone metastasis of a cancer develops.

Figure 19:
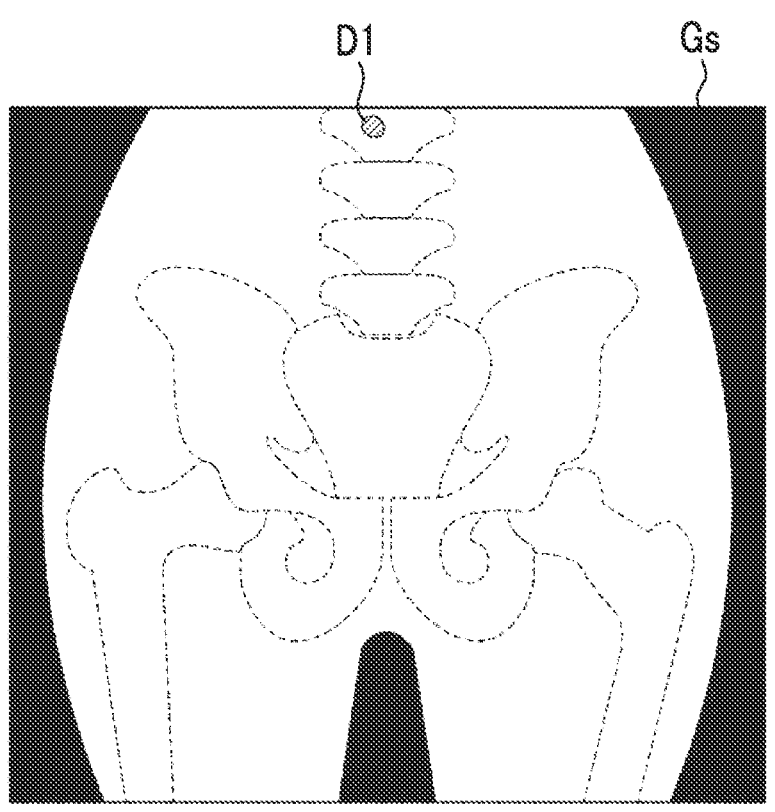
FIG. 19 is a diagram showing the soft part image of a patient in which a bone metastasis of a cancer occurs in a vertebra.

Here, in a case where the bone metastasis of the cancer occurs, the bone is brittle and easily fractures. Further, the cancer appears as a region having a higher density than the normal bone marrow. FIG. 19 is a diagram showing the soft part image of the patient in which the bone metastasis of the cancer occurs in the vertebra. As shown in FIG. 19, in the soft part image Gs, the cancer is metastatic to a fourth lumbar vertebra, and an elliptical high-density region DI is included. In FIG. 19, for the sake of description, the region DI having the high density is hatched.

In this case, the fracture probability, which is the correct answer data 42, can be calculated by obtaining, for the plurality of patients with developed bone metastasis of the cancer and with similar bone mineral density for each pixel of the target bone region and pixel value for each pixel of the corresponding region, the number of cases in which the fracture has occurred after the elapse of the predetermined number of years (for example, one year, two years, or five years) and dividing the obtained number of cases by the number of patients.

With the use of the pixel value of the corresponding region corresponding to the target bone (for example, fourth lumbar vertebra), which is included in the soft part image Gs as shown in FIG. 19, as the data for learning, it is possible to construct the trained neural network that derives the bone metastasis of the cancer. Therefore, with the application of such a trained neural network to the probability derivation unit 24, it is possible to derive the fracture probability due to the bone metastasis of the cancer. Further, with reference to the fracture probability, it is possible to detect the bone metastasis of the cancer at an early stage by using the simple radiation image.

Even in this case, of course, the simple radiation image may be further used as the data for learning of the training data.

Figure 20:
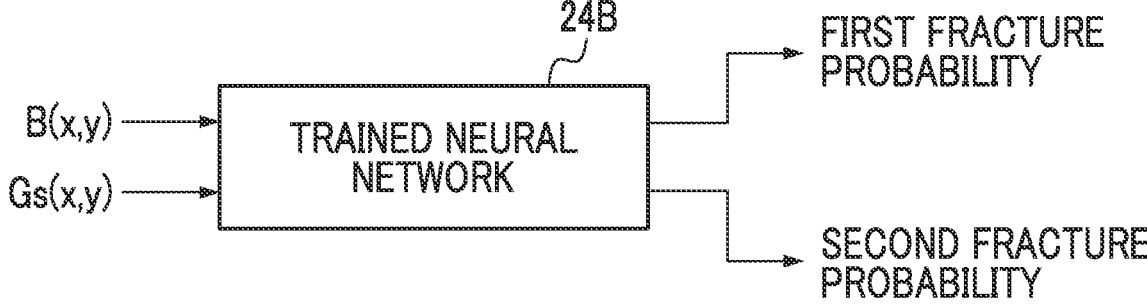
FIG. 20 is a diagram showing another example of the trained neural network.

Further, as shown in FIG. 20, it is also possible to derive a first fracture probability due to the initial fracture and a second fracture probability due to the bone metastasis of the cancer, from the bone mineral density B(x,y) of the target bone region in the bone part image Gb and the pixel value Gs(x,y) of the corresponding region in the soft part image Gs, using one trained neural network 24B. In this case, the training data (referred to as first training data) shown in FIG. 12 and the training data (referred to as second training data) including the pixel value of the corresponding regions in the soft part image Gs shown in FIG. 19 are prepared as the data for learning, and the data for learning of the pieces of training data is input to the neural network and the neural network is caused to output the fracture probability (referred to as first fracture probability) due to the initial fracture and the fracture probability (referred to as second fracture probability) due to the bone metastasis of the cancer. The learning of the neural network is performed such that the first fracture probability approaches one and the second fracture probability approaches zero in a case where the data for learning of the first training data is input. On the other hand, the learning of the neural network is performed such that the first fracture probability approaches zero and the second fracture probability approaches one in a case where the data for learning of the second training data is input. Accordingly, with the use of one trained neural network 24B, it is possible to derive both the fracture probability due to the initial fracture and the fracture probability due to the bone metastasis of the cancer.

Further, in the embodiment described above, the bone mineral density is derived by using the first radiation image G1 and the second radiation image G2 itself, but the present disclosure is not limited thereto. A moving average with surrounding pixels may be calculated for each pixel of the first radiation image G1 and the second radiation image G2, and the first radiation image G1 and the second radiation image G2 with the moving average as the pixel value of each pixel may be used to derive the bone mineral density. Here, since a cortical bone is important information in determining the bone mineral density, the moving average with surrounding pixels for each pixel may be calculated to maintain a resolution in which the cortical bone can be visually recognized, for example, a resolution of 2 mm or less in terms of an actual size of the subject. In this case, the pixels used for the moving average may be decided as appropriate from information on a mutual distance between the radiation source 3, the subject H, and the radiation detectors 5 and 6, information on a pixel size of the radiation detectors 5 and 6, and the like.

By the way, since a tube configuring the radiation source 3 deteriorates over time, the quality and the dose of the radiation emitted from the radiation source 3 change over time. As a result, the pixel value of the radiation image output from the radiation detectors 5 and 6 changes over time. Further, since the radiation detectors 5 and 6 also deteriorate over time, the pixel values of the first and second radiation images G1 and G2 output from the radiation detectors 5 and 6 change over time. In a case where the pixel values of the first and second radiation images G1 and G2 vary, an error occurs in the bone part image Gb and the soft part image Gs derived by Expression (1) and Expression (2). As a result, the bone tissue and the soft tissue do not all disappear and disappear too much. As described above, in a case where the accuracy of the bone part image Gb and the soft part image Gs is lowered, the bone mineral density and further the fracture probability cannot be derived with high accuracy.

Hereinafter, the reason why the error occurs in the bone part image Gb, particularly, will be described. In the present embodiment, while the processing of removing the scattered ray component is performed, the body thickness distribution is repeatedly derived to match the estimated image in performing the processing. In this case, for the body thickness, a pixel value I0 on an assumption that there is no subject H is used. The pixel value I0 is derived based on calibration data acquired in advance, using the tube voltage kv, the dose mAs, and the SID. For this reason, in a case where the quality and the dose of the radiation and a signal value output from the radiation detector are changed, as compared with a time at which the calibration data is acquired, an error occurs in the calculated pixel value I0. In a case where the error occurs in the pixel value I0 as described above, an error occurs in the derived body thickness, and as a result, an error occurs in the first and second radiation images G1 and G2 from which the scattered ray component is removed. Thus, the error occurs in the bone part image Gb and the soft part image Gs derived by Expression (1) and Expression (2).

Here, since the bone part image Gb has a composition different from the soft part image Gs, a correlation between the bone part image Gb and the soft part image Gs is small. On the other hand, in a case where the composition does not all disappear and disappears too much, the correlation between the bone part image Gb and the soft part image Gs is increased. For this reason, in the present embodiment, the bone part image Gb and the soft part image Gs may be derived such that the correlation between the bone part image Gb and the soft part image Gs is minimized. Hereinafter, the derivation of the bone part image Gb and the soft part image Gs having the minimum correlation will be described.

The information derivation unit 23 derives a provisional bone part image Gb0 and a provisional soft part image Gs0 by Expression (1) and Expression (2) described above. Here, with addition of the bone part image and the soft part image, the radiation image including both the bone part and the soft part is derived. This radiation image is referred to as an original radiation image G10. The original radiation image G10 is G10=Gb0+Gs0. In the present embodiment, a coefficient h0 for adjusting a level of disappearance of the bone in the provisional bone part image Gb0 is defined. The information derivation unit 23 multiplies the provisional bone part image Gb0 by the coefficient h0 to derive a new provisional bone part image Gb0. In this case, a new provisional soft part image Gs0 is derived by G10–Gb0. The information derivation unit 23 derives a correlation r between the new provisional bone part image Gb0 and the new provisional soft part image Gs0 by Expression (4) while changing a value of the coefficient h0. The coefficient h0 is derived as a uniform value for all the pixels. On the other hand, the coefficient h0 may be derived for each pixel in the image. In this case, the provisional bone part image Gb0 and the provisional soft part image Gs0 may be calculated by using the uniform value in a local region centered on the pixel for calculating the coefficient h0, and the correlation r may be derived by using the provisional bone part image Gb0 and the provisional soft part image Gs0 in the local region.

$$r = kbs/(db \cdot d) \tag{4}$$
$$= (1/n)\Sigma(bi - B) \cdot (si - S)/$$
$$\{\sqrt{((1/n)\Sigma(bi - B)^2)} \cdot \sqrt{((1/n)\rho(si - S)^2)}\}$$

In Expression (4), kbs is a covariance between the new provisional bone part image Gb0 and the new provisional soft part image Gs0, db is a standard deviation of the new provisional bone part image Gb0, ds is a standard deviation of the new provisional soft part image Gs0, n is the number of pixels of the new provisional bone part image Gb0 and the new provisional soft part image Gs0, bi and si are pixel values of respective pixels of the new provisional bone part image Gb0 and the new provisional soft part image Gs0, respectively, and B and S are average values of all pixels of the new provisional bone part image Gb0 and the new provisional soft part image Gs0, respectively. Although the image is two-dimensional, it is represented one-dimensionally by assigning a number to each pixel of the image in Expression (4).

The information derivation unit 23 derives the correlation r while changing the value of the coefficient h0, and multiplies the provisional bone part image Gb0 derived by Expression (1) by the coefficient h0 in a case where the correlation r is minimized to derive the bone part image Gb. That is, the information derivation unit 23 derives the bone part image Gb by Expression (5). Further, as shown in Expression (6), the information derivation unit 23 subtracts the bone part image Gb derived by Expression (5) from the original radiation image G10 to derive the soft part image Gs. In the present embodiment, although a plurality of correlations are derived by deriving the correlation r while changing the coefficient h0, the minimum correlation r means the correlation r having a minimum correlation among the plurality of derived correlations.

$$Gb = h0 \times Gb0 \tag{5}$$
$$Gs = G10 - Gb \tag{6}$$

Here, in a case where the correlation r is derived, the provisional bone part image Gb0 and the provisional soft part image Gs0 may be frequency-decomposed into band components consisting of a plurality of frequency bands, and the band component of a specific frequency band among the plurality of frequency bands may be used to derive the correlation r. The specific frequency band means one or more frequency bands set in advance among the plurality of frequency bands.

In this manner, with the derivation of the bone part image Gb and the soft part image Gs that have a minimum correlation with each other, it is possible to derive the high-accuracy bone part image Gb and soft part image Gs, in which the composition does not all disappear and disappears too much. Therefore, it is possible to derive the bone mineral density and the pixel value in the corresponding region with high accuracy, and as a result, derive the fracture probability of the target bone with higher accuracy.

Further, in each embodiment described above, the first and second radiation images G1 and G2 are acquired by the one-shot method in a case where the energy subtraction processing is performed, but the present disclosure is not limited thereto. The first and second radiation images G1 and G2 may be acquired by a so-called two-shot method in which imaging is performed twice by using only one radiation detector. In a case of the two-shot method, there is a possibility that a position of the subject H included in the first radiation image G1 and the second radiation image G2 deviates due to a body movement of the subject H. Therefore, in the first radiation image G1 and the second radiation image G2, it is preferable to perform the processing according to the present embodiment after registration of the subject is performed.

Further, in the embodiment described above, the bone disease prediction processing is performed by using the radiation image acquired by the system that images the first and second radiation images G1 and G2 of the subject H by using the first and second radiation detectors 5 and 6, it is needless to say that the technology of the present disclosure can be applied to even in a case where the first and second radiation images G1 and G2 are acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case where the first and second radiation images G1 and G2 are acquired by using the accumulative phosphor sheet.

Further, the radiation in the embodiments described above is not particularly limited, and α-rays or γ-rays can be used in addition to X-rays.

Further, in the embodiment described above, for example, as hardware structures of processing units that execute various kinds of processing, such as the image acquisition unit 21, the information acquisition unit 22, the information derivation unit 23, the probability derivation unit 24, the learning unit 25, and the display control unit 26, various processors shown below can be used. The various processors include a programmable logic device (PLD) which is a processor whose circuit configuration is changeable after manufacturing such as a field programmable gate array (FPGA), a dedicated electric circuit which is a processor having a circuit configuration exclusively designed to execute specific processing such as an application specific integrated circuit (ASIC), and the like, in addition to the CPU which is a general-purpose processor that executes software (program) to function as various processing units, as described above.

One processing unit may be configured by one of the various processors or a combination of two or more processors of the same type or different types (for example, a combination of a plurality of FPGAs or a combination of a CPU and an FPGA). Further, the plurality of processing units may be configured of one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as a hardware structure.

Further, more specifically, a circuitry combining circuit elements such as semiconductor elements can be used as the hardware structure of the various processors.

The supplementary notes of the present disclosure will be described below.

(Supplementary Note 1)

A bone disease prediction device comprising:

at least one processor, wherein the processor is configured to:

acquire a first radiation image and a second radiation image which are acquired by imaging a subject including a bone part and a soft part with radiation having different energy distributions;

perform weighting subtraction on the first radiation image and the second radiation image to derive a bone part image representing a bone tissue of the subject and a soft part image representing a soft tissue of the subject;

derive a bone mineral density for each pixel in a target bone region of the subject from the bone part image;

acquire a pixel value for each pixel of a corresponding region, which corresponds to the target bone region, in the soft part image; and derive a fracture probability of a target bone from the bone mineral density for each pixel in the target bone region and the pixel value for each pixel in the corresponding region.

(Supplementary Note 2)

The bone disease prediction device according to Supplementary Note 1, wherein the processor is configured to:

function as a trained neural network subjected to machine learning using, as training data, a bone mineral density for each pixel of a target bone region derived from a bone part image of a human body, a pixel value for each pixel of a corresponding region, which corresponds to the target bone region, derived from a soft part image of the human body, and correct answer data representing a fracture probability of the target bone.

(Supplementary Note 3)

The bone disease prediction device according to Supplementary Note 1, wherein the processor is configured to:

derive the fracture probability from the first radiation image or the second radiation image, in addition to the bone mineral density for each pixel in the target bone region and the pixel value for each pixel in the corresponding region.

(Supplementary Note 4)

The bone disease prediction device according to Supplementary Note 3, wherein the processor is configured to:

function as a trained neural network subjected to machine learning using, as training data, a simple radiation image of a human body, a bone mineral density for each pixel of the target bone derived from a bone part image of the human body, a pixel value for each pixel of a corresponding region, which corresponds to the target bone, derived from a soft part image of the human body, and correct answer data representing the fracture probability.

(Supplementary Note 5)

The bone disease prediction device according to any one of Supplementary Notes 1 to 4, wherein the processor is configured to:

display the fracture probability on a display.

(Supplementary Note 6)

The bone disease prediction device according to any one of Supplementary Notes 1 to 5, wherein the target bone is a femur.

(Supplementary Note 7)

The bone disease prediction device according to any one of Supplementary Notes 1 to 5, wherein the target bone is a vertebra.

(Supplementary Note 8)

The bone disease prediction device according to any one of Supplementary Notes 1 to 7, wherein the processor is configured to:

derive the bone part image and the soft part image that have a minimum correlation with each other.

(Supplementary Note 9)

The bone disease prediction device according to Supplementary Note 8, wherein the processor is configured to:

derive the bone part image and the soft part image such that a correlation of specific frequency components in the bone part image and the soft part image is minimized.

(Supplementary Note 10)

A learning device comprising:

at least one processor, wherein the processor is configured to:

perform machine learning on a neural network by using, as training data, a bone mineral density for each pixel of a target bone derived from a bone part image of a human body, a pixel value for each pixel of a corresponding region, which corresponds to the target bone, derived from a soft part image of the human body, and correct answer data representing a fracture probability of the target bone to construct a trained neural network that derives a fracture probability of the target bone of the target subject, from a bone mineral density for each pixel in a target bone region derived from a bone part image of a target subject and a pixel value for each pixel of a corresponding region, which corresponds to the target bone region, derived from a soft part image of the target subject.

(Supplementary Note 11)

The learning device according to Supplementary Note 10, wherein the processor is configured to:

perform the machine learning on the neural network by further using, as training data, a simple radiation image of the human body.

(Supplementary Note 12)

A trained neural network configured to derive, in a case where a bone mineral density for each pixel of a target bone region derived from a bone part image of a target subject and a pixel value for each pixel in a corresponding region, which corresponds to the target bone region, derived from a soft part image of the target subject are input, a fracture probability of a target bone of the target subject.

(Supplementary Note 13)

A trained neural network configured to derive, from a simple radiation image of a target subject, a bone mineral density for each pixel of a target bone region derived from a bone part image of the target subject, and a pixel value for each pixel in a corresponding region, which corresponds to the target bone region, derived from a soft part image of the target subject, a fracture probability of a target bone of the target subject.

(Supplementary Note 14)

A bone disease prediction method comprising:

acquiring a first radiation image and a second radiation image which are acquired by imaging a subject including a bone part and a soft part with radiation having different energy distributions;

performing weighting subtraction on the first radiation image and the second radiation image to derive a bone part image representing a bone tissue of the subject and a soft part image representing a soft tissue of the subject;

deriving a bone mineral density for each pixel in a target bone region of the subject from the bone part image;

acquiring a pixel value for each pixel of a corresponding region, which corresponds to the target bone region, in the soft part image; and deriving a fracture probability of a target bone from the bone mineral density for each pixel in the target bone region and the pixel value for each pixel in the corresponding region.

(Supplementary Note 15)

A learning method comprising:

performing machine learning on a neural network by using, as training data, a bone mineral density for each pixel of a target bone derived from a bone part image of a human body, a pixel value for each pixel of a corresponding region, which corresponds to the target bone, derived from a soft part image of the human body, and correct answer data representing a fracture probability of the target bone to construct a trained neural network that derives a fracture probability of the target bone of the target subject, from a bone mineral density for each pixel in a target bone region derived from a bone part image of a target subject and a pixel value for each pixel of a corresponding region, which corresponds to the target bone region, derived from a soft part image of the target subject.

(Supplementary Note 16)

A bone disease prediction program causing a computer to execute:

a procedure of acquiring a first radiation image and a second radiation image which are acquired by imaging a subject including a bone part and a soft part with radiation having different energy distributions;

a procedure of performing weighting subtraction on the first radiation image and the second radiation image to derive a bone part image representing a bone tissue of the subject and a soft part image representing a soft tissue of the subject;

a procedure of deriving a bone mineral density for each pixel in a target bone region of the subject from the bone part image;

a procedure of acquiring a pixel value for each pixel of a corresponding region, which corresponds to the target bone region, in the soft part image; and a procedure of deriving a fracture probability of a target bone from the bone mineral density for each pixel in the target bone region and the pixel value for each pixel in the corresponding region.

(Supplementary Note 17)

A learning program causing a computer to execute:

performing machine learning on a neural network by using, as training data, a bone mineral density for each pixel of a target bone derived from a bone part image of a human body, a pixel value for each pixel of a corresponding region, which corresponds to the target bone, derived from a soft part image of the human body, and correct answer data representing a fracture probability of the target bone to construct a trained neural network that derives a fracture probability of the target bone of the target subject, from a bone mineral density for each pixel in a target bone region derived from a bone part image of a target subject and a pixel value for each pixel of a corresponding region, which corresponds to the target bone region, derived from a soft part image of the target subject.

What is claimed is:

1. A bone disease prediction device comprising:

an imaging apparatus including a first radiation detector and a second radiation detector, the imaging apparatus acquiring a first radiation image and a second radiation image by imaging a subject including a bone part and a soft part with radiation having different energy distributions;

a display; and at least one processor, wherein the processor is configured to:

perform weighting subtraction on the first radiation image and the second radiation image to derive a bone part image representing a bone tissue of the subject and a soft part image representing a soft tissue of the subject;

derive a subject bone mineral density for each pixel in a subject bone region of the subject from the bone part image by correcting pixel values of the subject bone region in the bone part image using a correction coefficient acquired from a look-up table in accordance with an imaging condition and a body thickness distribution of the subject;

acquire a subject pixel value for each pixel of a corresponding subject marrow region in the soft part image, the corresponding subject marrow region being in the subject bone region;

derive a fracture probability of a target bone having the subject bone region and the corresponding subject marrow region by inputting the subject bone mineral density for each pixel in the subject bone region and the subject pixel value for each pixel in the corresponding subject marrow region into a trained neural network, the trained neural network outputting the fracture probability; and display the fracture probability on the display;

wherein the trained neural network has been subjected to machine learning using, as training data, a reference bone mineral density for each pixel of a reference bone region derived from a bone part image of a human body, a reference pixel value for each pixel of a corresponding reference marrow region, which is in the reference bone region, derived from a soft part image of the human body, and correct answer data representing a reference fracture probability of a reference bone of the human body, the reference bone of the human body having the reference bone region and the corresponding reference marrow region, wherein the trained neural network has been subjected to machine learning using the training data from a plurality of human bodies.

2. The bone disease prediction device according to claim 1, wherein the processor is configured to:

derive the fracture probability from the first radiation image or the second radiation image in addition to the subject bone mineral density for each pixel in the subject bone region and the subject pixel value for each pixel in the corresponding subject marrow region; and wherein the training data also includes a simple radiation image of the human body.

3. The bone disease prediction device according to claim 1, wherein the target bone is a femur.

4. The bone disease prediction device according to claim 1, wherein the target bone is a vertebra.

5. The bone disease prediction device according to claim 1, wherein the bone part image and the soft part image of the subject are derived to have a minimum correlation with each other.

6. The bone disease prediction device according to claim 1, wherein the processor is configured to:

derive the bone part image and the soft part image of the subject such that a correlation of specific frequency components in the bone part image and the soft part image is minimized.

7. A system for training a neural network to derive a fracture probability, the system comprising:

an imaging apparatus including a first radiation detector and a second radiation detector, the imaging apparatus acquiring a first radiation image and a second radiation image by imaging a subject including a bone part and a soft part with radiation having different energy distributions;

at least one processor, wherein the processor is configured to:

perform weighting subtraction on the first radiation image and the second radiation image to derive a bone part image representing a bone tissue of the subject and a soft part image representing a soft tissue of the subject;

derive a reference bone mineral density for each pixel in a reference bone region of the subject from the bone part image by correcting pixel values of the reference bone region in the bone part image using a correction coefficient acquired from a look-up table in accordance with an imaging condition and a body thickness distribution of the subject;

acquire a reference pixel value for each pixel of a corresponding reference marrow region in the soft part image, the corresponding reference marrow region being in the reference bone region;

perform machine learning on a neural network by using, as training data, a reference fracture probability of a reference bone as correct answer data, the reference bone mineral density for each pixel of the reference bone, and the reference pixel value for each pixel of the corresponding reference marrow region, to construct a trained neural network that derives a fracture probability of a target bone of a new subject, from a subject bone mineral density for each pixel in a subject bone region derived from a bone part image of the new subject and a subject pixel value for each pixel of a corresponding subject marrow region, which is in the subject bone region, derived from a soft part image of the new subject.

8. The system for training a neural network to derive a fracture probability according to claim 7, wherein the processor is configured to:

perform the machine learning on the neural network by further using, as training data, a simple radiation image of the human body.

9. A bone disease prediction method comprising:

acquiring a first radiation image and a second radiation image by imaging a subject including a bone part and a soft part with radiation having different energy distributions, wherein the first radiation image and the second radiation image are acquired by an imaging apparatus having a first radiation detector and a second radiation detector;

performing weighting subtraction on the first radiation image and the second radiation image to derive a bone part image representing a bone tissue of the subject and a soft part image representing a soft tissue of the subject;

deriving a subject bone mineral density for each pixel in a subject bone region of the subject from the bone part image by correcting pixel values of the subject bone region in the bone part image using a correction coefficient acquired from a look-up table in accordance with an imaging condition and a body thickness distribution of the subject;

acquiring a subject pixel value for each pixel of a corresponding subject marrow region in the soft part image, the corresponding subject marrow region being in the subject bone region; and deriving a fracture probability of a target bone having the subject bone region and the corresponding subject marrow region by inputting the subject bone mineral density for each pixel in the subject bone region and the subject pixel value for each pixel in the corresponding subject marrow region into a trained neural network, the trained neural network outputting the fracture probability, the trained neural network outputting the fracture probability; and displaying the fracture probability on a display;

wherein the trained neural network has been subjected to machine learning using, as training data, a reference bone mineral density for each pixel of a reference bone region derived from a bone part image of a human body, a reference pixel value for each pixel of a corresponding reference marrow region, which is in the reference bone region, derived from a soft part image of the human body, and correct answer data representing a reference fracture probability of a reference bone of the human body, the reference bone of the human body having the reference bone region and the corresponding reference marrow region, wherein the trained neural network has been subjected to machine learning using the training data from a plurality of human bodies.

10. A method for training a neural network to derive a fracture probability, the system comprising:

performing weighting subtraction on a first radiation image and a second radiation image to derive a bone part image representing a bone tissue of the subject and a soft part image representing a soft tissue of the subject, wherein the first radiation image and the second radiation image are acquired by imaging with radiation having different energy distributions;

deriving a reference bone mineral density for each pixel in a reference bone region of the subject from the bone part image by correcting pixel values of the reference bone region in the bone part image using a correction coefficient acquired from a look-up table in accordance with an imaging condition and a body thickness distribution of the subject;

acquiring a reference pixel value for each pixel of a corresponding reference marrow region in the soft part image, the corresponding reference marrow region being in the reference bone region; and performing machine learning on a neural network by using, as training data, a reference fracture probability of a reference bone as correct answer data, the reference bone mineral density for each pixel of the reference bone, and the reference pixel value for each pixel of the corresponding reference marrow region, to construct a trained neural network that derives a fracture probability of a target bone of a new subject, from a subject bone mineral density for each pixel in a subject bone region derived from a bone part image of the new subject and a subject pixel value for each pixel of a corresponding subject marrow region, which is in the subject bone region, derived from a soft part image of the new subject.

11. A non-transitory computer-readable storage medium that stores a bone disease prediction program causing a computer to execute:

a procedure of acquiring a first radiation image and a second radiation image by imaging a subject including a bone part and a soft part with radiation having different energy distributions, wherein the first radiation image and the second radiation image are acquired by an imaging apparatus having a first radiation detector and a second radiation detector;

a procedure of performing weighting subtraction on the first radiation image and the second radiation image to derive a bone part image representing a bone tissue of the subject and a soft part image representing a soft tissue of the subject;

a procedure of deriving a subject bone mineral density for each pixel in a subject bone region of the subject from the bone part image by correcting pixel values of the subject bone region in the bone part image using a correction coefficient acquired from a look-up table in accordance with an imaging condition and a body thickness distribution of the subject;

a procedure of acquiring a subject pixel value for each pixel of a corresponding subject marrow region in the soft part image, the corresponding subject marrow region being in the subject bone region;

a procedure of deriving a fracture probability of a target bone having the subject bone region and the corresponding subject marrow region by inputting the subject bone mineral density for each pixel in the subject bone region and the subject pixel value for each pixel in the corresponding subject marrow region into a trained neural network, the trained neural network outputting the fracture probability of the target bone; and a procedure of displaying the fracture probability on a display;

wherein the trained neural network has been subjected to machine learning using, as training data, a reference bone mineral density for each pixel of a reference bone region derived from a bone part image of a human body, a reference pixel value for each pixel of a corresponding reference marrow region, which is in the reference bone region, derived from a soft part image of the human body, and correct answer data representing a reference fracture probability of a reference bone of the human body, the reference bone of the human body having the reference bone region and the corresponding reference marrow region, wherein the trained neural network has been subjected to machine learning using the training data from a plurality of human bodies.

12. A non-transitory computer-readable storage medium that stores a learning program causing a computer to execute:

a procedure of performing weighting subtraction on a first radiation image and a second radiation image to derive a bone part image representing a bone tissue of the subject and a soft part image representing a soft tissue of the subject, wherein the first radiation image and the second radiation image are acquired by imaging with radiation having different energy distributions;

a procedure of deriving a reference bone mineral density for each pixel in a reference bone region of the subject from the bone part image by correcting pixel values of the reference bone region in the bone part image using a correction coefficient acquired from a look-up table in accordance with an imaging condition and a body thickness distribution of the subject;

a procedure of acquiring reference a pixel value for each pixel of a corresponding reference marrow region in the soft part image, the corresponding reference marrow region being in the reference bone region; and a procedure of performing machine learning on a neural network by using, as training data, a reference fracture probability of a reference bone as correct answer data, the reference bone mineral density for each pixel of the reference bone, and the reference pixel value for each pixel of the corresponding reference marrow region, to construct a trained neural network that derives a fracture probability of a target bone of a new subject, from a subject bone mineral density for each pixel in a subject bone region derived from a bone part image of the new subject and a subject pixel value for each pixel of a corresponding subject marrow region, which is in the subject bone region, derived from a soft part image of the new subject.

13. A trained neural network comprising a plurality of learned parameters, the trained neural network configured to:

receive, as inputs, a subject bone mineral density for each pixel in a subject bone region of a subject and a subject pixel value for each pixel in a subject marrow region corresponding to the subject bone region, the subject marrow region being in the subject bone region, the subject bone region and the subject marrow region being from a bone part image and a soft part image, respectively, that are derived by performing weighting subtraction of a first radiation image and a second radiation image of the subject that are acquired at different energy distributions;

derive, from the subject bone mineral densities and the subject pixel values of the subject, a fracture probability of a target bone having the subject bone region and the corresponding subject marrow region; and output the fracture probability;

wherein the plurality of learned parameters were generated by machine learning using training data from a plurality of human bodies, the training data comprising:

a reference bone mineral density for each pixel of a reference bone region derived from a bone part image of a human body, the reference bone region being derived by performing weighting subtraction on a first radiation image and a second radiation image of the human body that are acquired at different energy distributions, the reference bone mineral density for each pixel being derived by correcting pixel values of the reference bone region in the bone part image using a correction coefficient that is acquired from a look-up table in accordance with an imaging condition and a body thickness distribution of the human body;

a reference pixel value for each pixel of a reference marrow region corresponding to the bone region, the reference marrow region being in the reference bone region and being from a soft part image that is also derived from the weighting subtraction of the first radiation image and the second radiation image of the human body; and correct answer data representing a reference fracture probability of a reference bone of the human body, the reference bone of the human body having the reference bone region and the reference marrow region.

14. A trained neural network comprising a plurality of learned parameters, the trained neural network configured to:

receive, as inputs, a subject bone mineral density for each pixel in a subject bone region of a subject and a subject pixel value for each pixel in a subject marrow region corresponding to the subject bone region, the subject marrow region being in the subject bone region, the subject bone region and the subject marrow region being from a bone part image and a soft part image, respectively, that are derived by performing weighting subtraction of a first radiation image and a second radiation image of the subject that are acquired at different energy distributions, wherein the inputs also include a simple radiation image of a target bone of the subject;

derive, from the subject bone mineral densities and the subject pixel values of the subject and the simple radiation image, a fracture probability of the target bone having the subject bone region and the corresponding subject marrow region; and output the fracture probability;

wherein the plurality of learned parameters were generated by machine learning using training data from a plurality of human bodies, the training data comprising:

a simple radiation image of a reference bone of a human body;

a reference bone mineral density for each pixel of a reference bone region derived from a bone part image of the human body, the reference bone region being derived by performing weighting subtraction on a first radiation image and a second radiation image of the human body that are acquired at different energy distributions, the reference bone mineral density for each pixel being derived by correcting pixel values of the reference bone region in the bone part image using a correction coefficient that is acquired from a look-up table in accordance with an imaging condition and a body thickness distribution of the human body;

a reference pixel value for each pixel of a reference marrow region corresponding to the bone region, the reference marrow region being in the reference bone region and being from a soft part image that is also derived from the weighting subtraction of the first radiation image and the second radiation image of the human body; and correct answer data representing a reference fracture probability of the reference bone of the human body, the reference bone of the human body having the reference bone region and the reference marrow region.

* * * * *